United States Patent
Evsyukov et al.

(10) Patent No.: US 11,104,754 B2
(45) Date of Patent: Aug. 31, 2021

(54) ASYMMETRICALLY SUBSTITUTED BIS-ALKENYL DIPHENYL ETHERS, THEIR PREPARATION AND USE

(71) Applicant: Evonik Operations GmbH, Essen (DE)

(72) Inventors: Sergey Evsyukov, Ludwigshafen (DE); Tim Pohlmann, Nidderau (DE); Horst Stenzenberger, Heidelberg (DE); Matthijs Ter Wiel, Dossenheim (DE)

(73) Assignee: Evonik Operations GmbH, Essen (DE)

( * ) Notice: Subject to any disclaimer, the term of this patent is extended or adjusted under 35 U.S.C. 154(b) by 145 days.

(21) Appl. No.: 16/349,399

(22) PCT Filed: Oct. 27, 2017

(86) PCT No.: PCT/EP2017/077544
§ 371 (c)(1),
(2) Date: May 13, 2019

(87) PCT Pub. No.: WO2018/091253
PCT Pub. Date: May 24, 2018

(65) Prior Publication Data
US 2019/0367652 A1    Dec. 5, 2019

(30) Foreign Application Priority Data
Nov. 15, 2016  (EP) ..................................... 16198849

(51) Int. Cl.
| | |
|---|---|
| *C08F 222/40* | (2006.01) |
| *C07C 43/263* | (2006.01) |
| *C07C 43/275* | (2006.01) |
| *C08J 5/24* | (2006.01) |

(52) U.S. Cl.
CPC .......... *C08F 222/40* (2013.01); *C07C 43/263* (2013.01); *C07C 43/275* (2013.01); *C08J 5/24* (2013.01); *C08F 222/408* (2020.02); *C08F 2810/20* (2013.01); *C08J 2335/08* (2013.01)

(58) Field of Classification Search
CPC ... C07C 43/263; C07C 43/275; C07C 43/257; C07C 43/285; C07C 43/20; C07C 43/215; C08J 5/24; C08J 2335/08; C08F 222/40; C08F 2810/20
See application file for complete search history.

(56) References Cited

U.S. PATENT DOCUMENTS

| | | | | |
|---|---|---|---|---|
| 3,382,212 A | * | 5/1968 | Price ...................... | C08G 65/44 528/214 |
| 4,057,587 A | * | 11/1977 | Karrer .................... | A01N 31/16 568/636 |
| 4,288,583 A | | 9/1981 | Zahir et al. | |
| 4,364,875 A | * | 12/1982 | Sehring ................. | C07C 231/12 558/414 |
| 4,371,719 A | | 2/1983 | Zahir et al. | |
| 4,419,124 A | * | 12/1983 | Swithenbank ......... | A01N 33/22 504/198 |
| 4,737,568 A | * | 4/1988 | Stenzenberger ....... | C08G 73/12 524/606 |
| 5,552,071 A | * | 9/1996 | Rudnick ................. | C07C 15/16 508/581 |
| 2009/0170927 A1 | * | 7/2009 | Bezwada ............... | C08G 63/66 514/455 |

OTHER PUBLICATIONS

International Search Report and Written Opinion dated Nov. 23, 2017 in PCT/EP2017/077544 filed Oct. 27, 2017.
Yada Bharath, et al., "An Efficient Synthesis of Dibenzo[b, f]oxepins by Ring-Closing Metathesis," Asian Journal of Organic Chemistry, vol. 2, XP055342144, 2013, pp. 848-851.
Sara A. L. Madeiro, et al., "New Neolignans from Krameria tomentosa A. St.-Hil," Journal of the Brazilian Chemical Society, vol. 23, No. 11, XP055342437, 2012, pp. 2021-2026.

* cited by examiner

*Primary Examiner* — Jane L Stanley
(74) *Attorney, Agent, or Firm* — Oblon, McClelland, Maier & Neustadt, L.L.P.

(57) ABSTRACT

The present invention relates to compounds according to formula (I) and to heat-curable resin compositions based on polymaleimide resin systems comprising such compounds as co-monomers: wherein $R^1$ signifies an 1-alkenyl- or 2-alkenyl group with 3 to 6 carbon atoms, wherein $R^2$ signifies hydrogen or an alkoxy group with up to 2 carbon atoms, wherein $R^3$ signifies hydrogen or an alkyl group with up to 4 carbon atoms, and wherein $R^4$ signifies hydrogen or an alkyl group with up to 4 carbon atoms. The present invention also relates to crosslinked resins obtainable by curing such compositions. Compounds of the present invention can be used amongst others in fields like structural adhesives, matrix resins for fiber prepregs, moulding compounds, as well as structural and/or electrical composites.

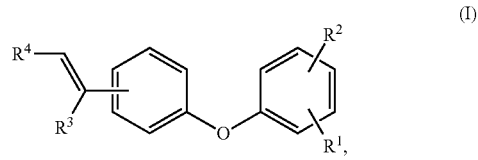

(I)

19 Claims, No Drawings

ASYMMETRICALLY SUBSTITUTED BIS-ALKENYL DIPHENYL ETHERS, THEIR PREPARATION AND USE

FIELD OF THE INVENTION

The present invention relates to asymmetrically substituted bis-alkenyl diphenyl ethers and to heat-curable resin compositions based on polymaleimide resin systems comprising such asymmetrically substituted bis-alkenyl diphenyl ethers as co-monomers. The present invention also relates to crosslinked resins obtainable by curing such compositions. Compounds of the present invention can be used amongst others in the following fields: Structural adhesives, matrix resins for fiber prepregs, moulding compounds, as well as structural and/or electrical composites.

BACKGROUND

Curable thermosetting compositions based on polymaleimide building blocks and co-monomers are established resins for fiber composites, adhesives, moulding and potting compounds. These resins are known for their high temperature resistance.

The co-monomer part of the composition influences several uncured and cured resin properties. Importantly, a suitable choice of this co-monomer part is required for modifying the processing properties of the uncured resin, in particular to adjust rheological properties such as flow and viscosity and to influence the cure kinetic properties.

Desired properties of the cured polymaleimide/co-monomer system include high glass transition temperature (Tg), high modulus retention at temperatures around 250° C., high heat resistance in terms of thermal oxidative stability (TOS) and durability, high toughness and damage tolerance and temperature cycling resistance to microcracking. Further desired properties include low moisture and solvent uptake and low dielectric constant (DC).

Many chemical concepts have been devised for generating polymaleimide/co-monomer systems. For applications as resins for fiber reinforced composites, structural adhesives and electrical and electronic appliances polymaleimide/alkenylphenol and polymaleimide/alkenylphenoxy based systems were found to be the most successful.

Alkenylphenol co-monomers are disclosed in U.S. Pat. No. 4,100,140 (1978).

Curable thermosetting compositions based on polymaleimides and alkenylphenoxy compounds are known, for example, from U.S. Pat. No. 4,789,704 (1988), 4,826,929 (1989), 4,808,717 (1989), 4962,161 (1990), 5,120,824 (1992), 4,873,284 (1989), 5,023,310 (1991), 5,023, 310 (1991), 5,070,154 (1991) as well as US 2008/0075965A1 (2008) and CN104628544A (2015).

Desirable properties of uncured bismaleimide/co-monomer systems with respect to their use for composites and fiber reinforced composites in particular, include low viscosity at processing temperature, low processing temperature, sufficient pot life at processing temperature, good storage stability in the form of resins and intermediate products such as prepregs, glues or compounds as well as fast cure kinetics (fast reaction of co-monomers and polymaleimides) during manufacture of composites.

Few investigations relating to fast curing bismaleimide/co-monomer systems have been conducted so far, which is unfortunate in view of the fact that fast cure kinetics enable curing in short periods of time thus facilitating processing to be performed in an advantageous manner. U.S. Pat. No. 4,288,583 (Zahir, Wyler, 1981) discloses the results of one such investigation. In particular, U.S. Pat. No. 4,288,583 discloses mixtures of polymaleimides und propenyl-substituted phenols, e.g. o,o'-di(1-propenyl)bisphenols, as fast curing polymaleimide/co-monomer systems. CN104628544A (Liu et al., 2015) as well is directed at fast curing systems and discloses polymaleimide/trifunctional propenyl-endcapped co-monomer systems which provide fast curing kinetics due to their triplicate functionality.

Cured products obtained from the bismaleimide/co-monomer systems disclosed in U.S. Pat. No. 4,288,583, however, exhibit a pronounced tendency to absorb water (particularly pronounced under hot/wet conditions) resulting in several disadvantageous characteristics of the respective products, including the following: lowered glass transition temperature (Tg), weakened mechanical properties at elevated temperatures, increased tendency to suffer from microcracks under conditions of thermal cycling when used in fibre reinforced composites, impared electrical properties (increased dielectric constant).

In view of the above an object of the present invention resided in providing co-monomers for use in polymaleimide/co-monomer systems which are low viscosity liquids or honey like fluids at room temperature in order to allow easy processing, i.e. easy blending with the polymaleimide to prepare the polymaleimide/co-monomer curable mixtures.

A further object of the present invention resided in providing co-monomers for use in polymaleimide/co-monomer systems as well as such polymaleimide/co-monomer systems characterized by fast cure kinetics (fast reaction of co-monomers and polymaleimides) and yielding copolymers with a low tendency to absorb water thus resulting in copolymers with (i) good mechanical properties at elevated temperatures and/or (ii) a low tendency to suffer from microcracks under conditions of thermal cycling and/or (iii) good electrical properties (low dielectric constant).

DETAILED DESCRIPTION OF THE INVENTION

This object is achieved by asymmetrically substituted bis-alkenyl diphenyl ethers of formula (I)

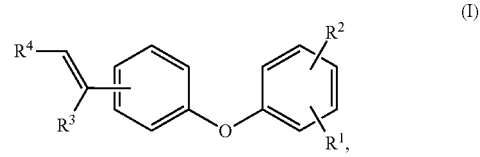

wherein $R^1$ signifies an 1-alkenyl- or 2-alkenyl group with 3 to 6 carbon atoms, wherein $R^2$ signifies hydrogen or an alkoxy group with up to 2 carbon atoms, wherein $R^3$ signifies hydrogen or an alkyl group with up to 4 carbon atoms, and wherein $R^4$ signifies hydrogen or an alkyl group with up to 4 carbon atoms with the proviso that (I) is not naturally occurring ottomentosa (1-methoxy-4-(1E)-1-propen-1-yl-2-[4-(1E)-1-propen-1-ylphenoxy]-benzene).

Ottomentosa (1-methoxy-4-(1E)-1-propen-1-yl-2-[4-(1E)-1-propen-1-ylphenoxy]-benzene, CAS No. 1469981-57-4) is a compound isolated from the roots of *Krameria tomentosa* A. St.-Hil., popularly known as "rhatany" (described in S. A. L. Madeiro, H. F. S. de Lucena, C. D. Siqueira, M. C. Duarte, R. Braz-Filho, J. M. Barbosa Filho, M. S. da Silva, J. F. Tavares: New Neolignans from *Krameria tomentosa* A. St.-Hil//J. Braz. Chem. Soc., 2012, Vol. 23, No. 11, 2021-2026).

In further preferred embodiments of the present invention, the 1-alkenyl group carrying substituents $R^3$ and $R^4$ in formula (I), is in the para position as indicated by formula (Ia)

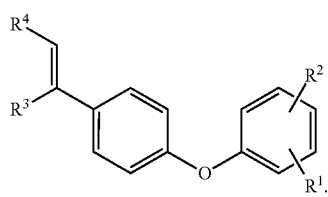

(Ia)

Preferred compounds according to formula (Ia) are:
4-vinyl-2'-(prop-1-en-1-yl)-diphenylether,
4-isopropenyl-2'-(prop-1-en-1-yl)-diphenylether,
4-(prop-1-en-1-yl)-2'-(prop-1-en-1-yl)-diphenylether,
4-(but-1-en-1-yl)-2'-(prop-1-en-1-yl)-diphenylether,
4-(pent-1-en-1-yl)-2'-(prop-1-en-1-yl)-diphenylether,
4-(1-methylprop-1-en-1-yl)-2'-(prop-1-en-1-yl)-diphenylether,
4-(1-methylbut-1-en-1-yl)-2'-(prop-1-en-1-yl)-diphenylether,
4-(1-methylpent-1-en-1-yl)-2'-(prop-1-en-1-yl)-diphenylether,
4-(1-ethylprop-1-en-1-yl)-2'-(prop-1-en-1-yl)-diphenylether,
4-(1-ethylbut-1-en-1-yl)-2'-(prop-1-en-1-yl)-diphenylether,
4-(1-ethylpent-1-en-1-yl)-2'-(prop-1-en-1-yl)-diphenylether,
4-vinyl-2'-methoxy-4'-(prop-1-en-1-yl)-diphenylether,
4-isopropenyl-2'-methoxy-4'-(prop-1-en-1-yl)-diphenylether,
4-(prop-1-en-1-yl)-2'-methoxy-4'-(prop-1-en-1-yl)-diphenylether,
4-(but-1-en-1-yl)-2'-methoxy-4'-(prop-1-en-1-yl)-diphenylether,
4-(pent-1-en-1-yl)-2'-methoxy-4'-(prop-1-en-1-yl)-diphenylether,
4-(1-methylprop-1-en-1-yl)-2'-methoxy-4'-(prop-1-en-1-yl)-diphenylether,
4-(1-methylbut-1-en-1-yl)-2'-methoxy-4'-(prop-1-en-1-yl)-diphenylether,
4-(1-methylpent-1-en-1-yl)-2'-methoxy-4'-(prop-1-en-1-yl)-diphenylether,
4-(1-ethylprop-1-en-1-yl)-2'-methoxy-4'-(prop-1-en-1-yl)-diphenylether,
4-(1-ethylbut-1-en-1-yl)-2'-methoxy-4'-(prop-1-en-1-yl)-diphenylether,
4-(1-ethylpent-1-en-1-yl)-2'-methoxy-4'-(prop-1-en-1-yl)-diphenylether,
4-vinyl-2'-ethoxy-5'-(prop-1-en-1-yl)-diphenylether,
4-isopropenyl-2'-ethoxy-5'-(prop-1-en-1-yl)-diphenylether,
4-(prop-1-en-1-yl)-2'-ethoxy-5'-(prop-1-en-1-yl)-diphenylether,
4-(but-1-en-1-yl)-2'-ethoxy-5'-(prop-1-en-1-yl)-diphenylether,
4-(pent-1-en-1-yl)-2'-ethoxy-5'-(prop-1-en-1-yl)-diphenylether,
4-(1-methylprop-1-en-1-yl)-2'-ethoxy-5'-(prop-1-en-1-yl)-diphenylether,
4-(1-methylbut-1-en-1-yl)-2'-ethoxy-5'-(prop-1-en-1-yl)-diphenylether,
4-(1-methylpent-1-en-1-yl)-2'-ethoxy-5'-(prop-1-en-1-yl)-diphenylether,
4-(1-ethylprop-1-en-1-yl)-2'-ethoxy-5'-(prop-1-en-1-yl)-diphenylether,
4-(1-ethylbut-1-en-1-yl)-2'-ethoxy-5'-(prop-1-en-1-yl)-diphenylether,
4-(1-ethylpent-1-en-1-yl)-2'-ethoxy-5'-(prop-1-en-1-yl)-diphenylether.

In further preferred embodiments of the present invention, the 1-alkenyl group carrying substituents $R^3$ and $R^4$ in formula (I), is in the para position and 1-alkenyl group $R^1$ is in the ortho position while $R^2$ is hydrogen, as indicated by formula (Ib)

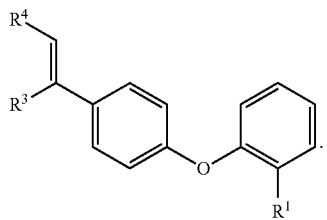

Preferred compounds according to formula (Ib) are:
4-vinyl-2'-(prop-1-en-1-yl)-diphenylether,
4-isopropenyl-2'-(prop-1-en-1-yl)-diphenylether,
4-(prop-1-en-1-yl)-2'-(prop-1-en-1-yl)-diphenylether,
4-(but-1-en-1-yl)-2'-(prop-1-en-1-yl)-diphenylether,
4-(pent-1-en-1-yl)-2'-(prop-1-en-1-yl)-diphenylether,
4-(1-methylprop-1-en-1-yl)-2'-(prop-1-en-1-yl)-diphenylether,
4-(1-methylbut-1-en-1-yl)-2'-(prop-1-en-1-yl)-diphenylether,
4-(1-methylpent-1-en-1-yl)-2'-(prop-1-en-1-yl)-diphenylether,
4-(1-ethylprop-1-en-1-yl)-2'-(prop-1-en-1-yl)-diphenylether,
4-(1-ethylbut-1-en-1-yl)-2'-(prop-1-en-1-yl)-diphenylether,
4-(1-ethylpent-1-en-1-yl)-2'-(prop-1-en-1-yl)-diphenylether.

In further preferred embodiments of the present invention, the 1-alkenyl group carrying substituents $R^3$ and $R^4$ in formula (I), is in the para position and 1-alkenyl group $R^1$ is in the para-position and $R^2$ is methoxy in the ortho-position, as indicated by formula (Ic)

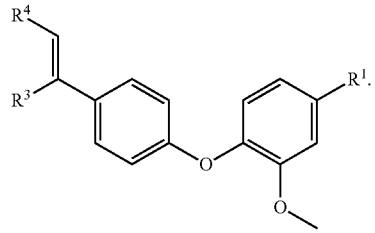

(Ic)

Preferred compounds according to formula (Ic) are:
4-vinyl-2'-methoxy-4'-(prop-1-en-1-yl)-diphenylether, 4-isopropenyl-2'-methoxy-4'-(prop-1-en-1-yl)-dip henylether,
4-(prop-1-en-1-yl)-2'-methoxy-4'-(prop-1-en-1-yl)-diphenylether,
4-(but-1-en-1-yl)-2'-methoxy-4'-(prop-1-en-1-yl)-diphenylether,
4-(pent-hylprop-1-en-1-y-y)-2'-methoxy-4'-(prop-1-en-1-1-y)-diphenylether,
4-(1-methylprop-1-en-1-yl)-2'-methoxy-4'-(prop-1-en-1-yl)-diphenylether,
4-(1-methylbut-1-en-1-yl)-2'-methoxy-4'-(prop-1-en-1-yl)-diphenylether,
4-(1-methylpent-1-en-1-yl)-2'-methoxy-4'-(prop-1-en-1-yl)-diphenylether,
4-(1-ethylprop-1-en-1-yl)-2'-methoxy-4'-(prop-1-en-1-yl)-diphenylether,
4-(1-ethylbut-1-en-1-yl)-2'-methoxy-4'-(prop-1-en-1-yl)-diphenylether,
4-(1-ethylpent-1-en-1-yl)-2'-methoxy-4'-(prop-1-en-1-yl)-diphenylether.

In further preferred embodiments of the present invention, the 1-alkenyl group carrying substituents $R^3$ and $R^4$ in formula (I), is in the para position and 1-alkenyl group $R^1$ is in the meta-position and $R^2$ is ethoxy in the ortho-position, as indicated by formula (Id)

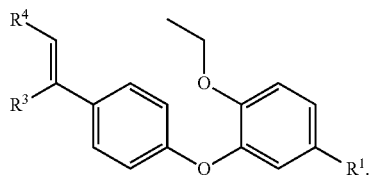

(Id)

Preferred compounds according to formula (Id) are:
4-vinyl-2'-ethoxy-5'-(prop-1-en-1-yl)-diphenylether,
4-isopropenyl-2'-ethoxy-5'-(prop-1-en-1-yl)-diphenylether,
4-(prop-1-en-1-yl)-2'-ethoxy-5'-(prop-1-en-1-yl)-diphenylether,
4-(but-1-en-1-yl)-2'-ethoxy-5'-(prop-1-en-1-yl)-diphenylether,
4-(pent-1-en-1-yl)-2'-ethoxy-5'-(prop-1-en-1-yl)-diphenylether,
4-(1-methylprop-1-en-1-yl)-2'-ethoxy-5'-(prop-1-en-1-yl)-diphenylether,
4-(1-methylbut-1-en-1-yl)-2'-ethoxy-5'-(prop-1-en-1-yl)-diphenylether,
4-(1-methylpent-1-en-1-yl)-2'-ethoxy-5'-(prop-1-en-1-yl)-diphenylether,
4-(1-ethylprop-1-en-1-yl)-2'-ethoxy-5'-(prop-1-en-1-yl)-diphenylether,
4-(1-ethylbut-1-en-1-yl)-2'-ethoxy-5'-(prop-1-en-1-yl)-diphenylether,
4-(1-ethylpent-1-en-1-yl)-2'-ethoxy-5'-(prop-1-en-1-yl)-diphenylether.

Curable Compositions of the Invention

In another aspect the present invention further relates to curable compositions comprising:
i) at least one asymmetrically substituted bis-alkenyl diphenyl ether of formula (I)

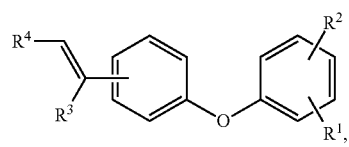

(I)

wherein $R^1$ signifies an 1-alkenyl- or 2-alkenyl group with up to 6 carbon atoms,
wherein $R^2$ signifies hydrogen or an alkoxy group with up to 2 carbon atoms,
wherein $R^3$ signifies hydrogen or an alkyl group with up to 4 carbon atoms, and
wherein $R^4$ signifies an alkyl group with up to 4 carbon atoms; and ii) at least one polyimide of formula (II)

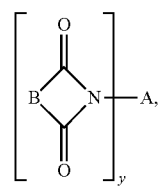

(II)

wherein
B is a difunctional group containing a carbon-carbon double bond, and
A is a y-functional group; and
y is an integer $\geq 2$.

In preferred curable compositions of the present invention the y-functional group A in the polyimide according to formula (II), is selected from the following difunctional groups:
a) alkylene group with 2 to 12 carbon atoms;
b) cycloalkylene group with 5 to 6 carbon atoms;
c) heterocyclic group with 4 to 5 carbon atoms and at least one nitrogen, oxygen, or sulphur atom in the ring;
d) mono- or dicarbocyclic group;
e) bridged multicyclic group consisting of at least two groups selected from monocarbocyclic aromatic groups, dicarbocyclic aromatic groups, cycloalkylene groups; wherein these groups are linked to each other by direct carbon-carbon bonds or by divalent groups; wherein preferably the divalent groups are selected from: oxy-group, thio-group, alkylene-group with 1 to 3 carbon atoms, sulfone-group, methanone-group, or one of the following groups

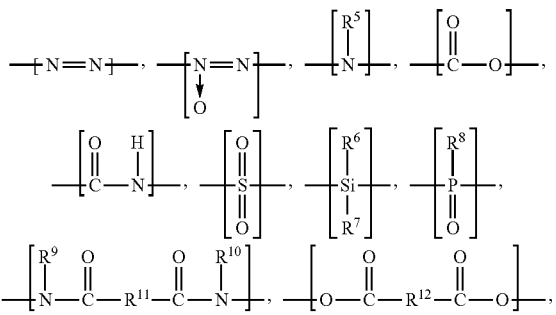

wherein $R^5$, $R^6$, $R^7$, $R^8$, $R^9$, $R^{10}$ are independently an alkyl group with 1 to 6 carbon atoms; and
$R^{11}$ and $R^{12}$ are independently an alkylene group with 1 to 6 carbon atoms;
f) group defined by formula (III)

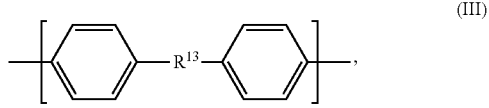

wherein $R^{13}$ is one of the following groups

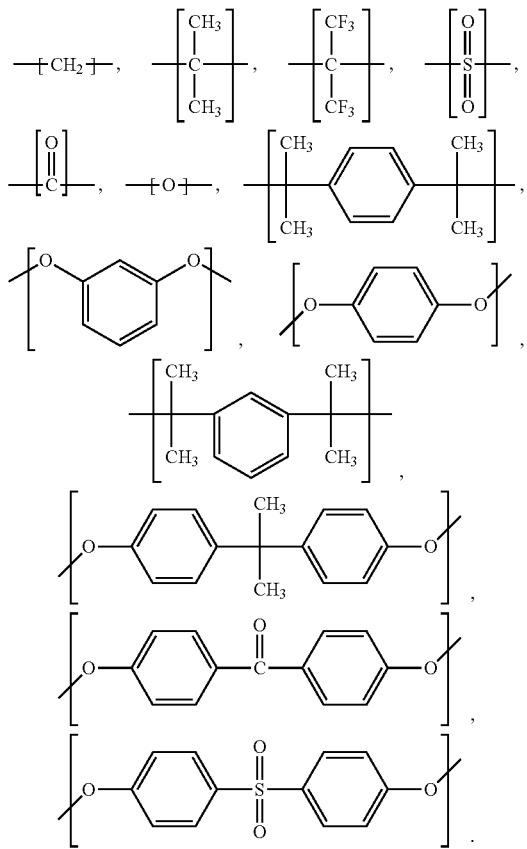

In preferred curable compositions of the present invention B in the polyimide according to formula (II), is selected from the following difunctional groups:

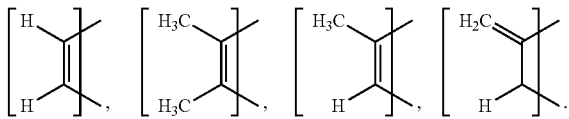

In further preferred curable compositions of the present invention the polyimide according to formula (II) is selected from:
4,4'-bismaleimidodiphenylmethane, bis(3-methyl-5-ethyl-4-maleimidophenyl)methane, bis(3,5-dimethyl-4-maleimidophenyl)methane, 4,4'-bismaleimidodiphenylether, 4,4'-bismaleimidodiphenylsulfone, 3,3'-bismaleimidodiphenylsulfone, bismaleimidodiphenylindane, 2,4-bismaleimidotoluene, 2,6-bismaleimidotoluene, 1,3-bismaleimidobenzene, 1,2-bismaleimidobenzene, 1,4-bismaleimidobenzene, 1,2-bismaleimidoethane, 1,6-bismaleimidohexane, 1,6-bismaleimido-(2,2,4-trimethyl)hexane, 1,6-bismaleimido-(2,4,4-trimethyl)hexane, 1,4-bis(maleimidomethyl)cyclohexane, 1,3-bis(maleimidomethyl)cyclohexane, 1,4-bismaleimidodicyclohexylmethane, 1,3-bis(maleimidomethyl)benzene, 1,4-bis(maleimidomethyl)benzene.

In further preferred curable compositions of the present invention $R^1$ in formula (I) is selected from 1-alkenyl groups with 2 to 6 carbon atoms,
and the polyimide according to formula (II) is selected from:
4,4'-bismaleimidodiphenylmethane, bis(3-methyl-5-ethyl-4-maleimidophenyl)methane, bis(3,5-dimethyl-4-maleimidophenyl)methane, 4,4'-bismaleimidodiphenylether, 4,4'-bismaleimidodiphenylsulfone, 3,3'-bismaleimidodiphenylsulfone, bismaleimidodiphenylindane, 2,4-bismaleimidotoluene, 2,6-bismaleimidotoluene, 1,3-bismaleimidobenzene, 1,2-bismaleimidobenzene, 1,4-bismaleimidobenzene, 1,2-bismaleimidoethane, 1,6-bismaleimidohexane, 1,6-bismaleimido-(2,2,4-trimethyl)hexane, 1,6-bismaleimido-(2,4,4-trimethyl)hexane, 1,4-bis(maleimidomethyl)cyclohexane, 1,3-bis(maleimidomethyl)cyclohexane, 1,4-bismaleimidodicyclohexylmethane, 1,3-bis(maleimidomethyl)benzene, 1,4-bis(maleimidomethyl)benzene.

In further preferred curable compositions of the present invention the asymmetrically substituted bis-alkenyl diphenyl ether according to formula (I) is selected from:
4-vinyl-2'-(prop-1-en-1-yl)-diphenylether,
4-isopropenyl-2'-(prop-1-en-1-yl)-diphenylether,
4-(prop-1-en-1-yl)-2'-(prop-1-en-1-yl)-diphenylether,
4-(but-1-en-1-yl)-2'-(prop-1-en-1-yl)-diphenylether,
4-(pent-1-en-1-yl)-2'-(prop-1-en-1-yl)-diphenylether,
4-(1-methylprop-1-en-1-yl)-2'-(prop-1-en-1-yl)-diphenylether,
4-(1-methylbut-1-en-1-yl)-2'-(prop-1-en-1-yl)-diphenylether,
4-(1-methylpent-1-en-1-yl)-2'-(prop-1-en-1-yl)-diphenylether,
4-(1-ethylprop-1-en-1-yl)-2'-(prop-1-en-1-yl)-diphenylether,
4-(1-ethylbut-1-en-1-yl)-2'-(prop-1-en-1-yl)-diphenylether,
4-(1-ethylpent-1-en-1-yl)-2'-(prop-1-en-1-yl)-diphenylether,
4-vinyl-2'-methoxy-4'-(prop-1-en-1-yl)-diphenylether,
4-isopropenyl-2'-methoxy-4'-(prop-1-en-1-yl)-diphenylether,
4-(prop-1-en-1-yl)-2'-methoxy-4'-(prop-1-en-1-yl)-diphenylether,
4-(but-1-en-1-yl)-2'-methoxy-4'-(prop-1-en-1-yl)-diphenylether,
4-(pent-1-en-1-yl)-2'-methoxy-4'-(prop-1-en-1-yl)-diphenylether,
4-(1-methylprop-1-en-1-yl)-2'-methoxy-4'-(prop-1-en-1-yl)-diphenylether,
4-(1-methylbut-1-en-1-yl)-2'-methoxy-4'-(prop-1-en-1-yl)-diphenylether,
4-(1-methylpent-1-en-1-yl)-2'-methoxy-4'-(prop-1-en-1-yl)-diphenylether,
4-(1-ethylprop-1-en-1-yl)-2'-methoxy-4'-(prop-1-en-1-yl)-diphenylether, 4-(1-ethylbut-1-en-1-yl)-2'-methoxy-4'-(prop-1-en-1-yl)-diphenylether,
4-(1-ethylpent-1-en-1-yl)-2'-methoxy-4'-(prop-1-en-1-yl)-diphenylether
4-vinyl-2'-ethoxy-5'-(prop-1-en-1-yl)-diphenylether,
4-isopropenyl-2'-ethoxy-5'-(prop-1-en-1-yl)-diphenylether,
4-(prop-1-en-1-yl)-2'-ethoxy-5'-(prop-1-en-1-yl)-diphenylether,
4-(but-1-en-1-yl)-2'-ethoxy-5'-(prop-1-en-1-yl)-diphenylether,
4-(pent-1-en-1-yl)-2'-ethoxy-5'-(prop-1-en-1-yl)-diphenylether,
4-(1-methylprop-1-en-1-yl)-2'-ethoxy-5'-(prop-1-en-1-yl)-diphenylether,
4-(1-methylbut-1-en-1-yl)-2'-ethoxy-5'-(prop-1-en-1-yl)-diphenylether,
4-(1-methylpent-1-en-1-yl)-2'-ethoxy-5'-(prop-1-en-1-yl)-diphenylether,
4-(1-ethylprop-1-en-1-yl)-2'-ethoxy-5'-(prop-1-en-1-yl)-diphenylether,
4-(1-ethylbut-1-en-1-yl)-2'-ethoxy-5'-(prop-1-en-1-yl)-diphenylether,
4-(1-ethylpent-1-en-1-yl)-2'-ethoxy-5'-(prop-1-en-1-yl)-diphenylether;
and the polyimide according to formula (II) is selected from:
4,4'-bismaleimidodiphenylmethane, bis(3-methyl-5-ethyl-4-maleimidophenyl)methane, bis(3,5-dimethyl-4-maleimidophenyl)methane, 4,4'-bismaleimidodiphenylether, 4,4'-bismaleimidodiphenylsulfone, 3,3'-bismaleimidodiphenylsulfone, bismaleimidodiphenylindane, 2,4-bismaleimidotoluene, 2,6-bismaleimidotoluene, 1,3-bismaleimidobenzene, 1,2-bismaleimidobenzene, 1,4-bismaleimidobenzene, 1,2-bismaleimidoethane, 1,6-bismaleimidohexane, 1,6-bismaleimido-(2,2,4-trimethyl)hexane, 1,6-bismaleimido-(2,4,4-trimethyl)hexane, 1,4-bis(maleimidomethyl)cyclohexane, 1,3-bis(maleimidomethyl)cyclohexane, 1,4-bismaleimidodicyclohexylmethane, 1,3-bis(maleimidomethyl)benzene, 1,4-bis(maleimidomethyl)benzene.

In another embodiment the present invention further relates to curable compositions as defined above further comprising one or more cure inhibitors to retard the polymerisation reaction, thus modifying processability and storage stability of the compositions and intermediate products, such as prepregs, moulding compounds and resin solutions. Suitable cure inhibitors are Hydroquinone, 1,4-Naphthoquinone, Ionole and Phenothiazine which are used at concentrations between 0.1 wt % and 2.0 wt %, based on the total weight of the composition. It is advantageous to dissolve the inhibitor in one of the components prior to the preparation of the mixture.

In another embodiment the present invention further relates to curable compositions as defined above further comprising one or more cure accelerators in order to accelerate the curing process. Typically cure accelerators are added in an amount of 0.01 wt % to 5 wt %, preferably in an amount of 0.1 wt % to 2 wt % based on the total weight of the curable composition. Suitable cure accelerators include ionic and free radical polymerization catalysts. Examples for free radical polymerization catalysts include (a) organic peroxides such as ditertiary butyl peroxide, diamylperoxide and t-butylperbenzoate and (b) azo compounds such as azobisisobutyronitrile. Examples of ionic catalysts are alkali metal compounds, tertiary amines such as triethylamine, dimethylbenzylamine, dimethylaniline, azabicyclooctane, heterocyclic amines such as quinoline, N-methylmorpholine, methylimidazole and phenylimidazole and phosphorous compounds such as triphenylphosphine and quaternary phosphonium halides. The cure accelerators can be admixed with the components of the curable composition or may be added during the production of the prepolymers either by a powder blending process or by a solvent blending process.

Curable Compositions Comprising a Secondary Co-Monomer Component

In another aspect the present invention further relates to curable compositions comprising in addition to the at least one asymmetrically substituted bis-alkenyl diphenyl ether according to formula (I) as defined above and the at least one polyimide of formula (II) as defined above, a secondary co-monomer component, which consists of one or a combination of at least two co-monomers selected from alkenylphenol, alkenylphenyl ether, alkenyl phenol ether, polyamine, aminophenol, aminoacid hydrazide, cyanate ester, diallyl phthalate, triallyl isocyanurate, triallyl cyanurate, styrene, divinylbenzene, wherein the secondary co-monomer component represents between 1 wt % and 30 wt % of the total composition.

These secondary co-monomers may act as diluents for the compositions of the invention modifying their viscosity and/or processability. The secondary co-monomers may also act as cure accelerators or as cure retardants in the compositions of the invention.

Preferably the secondary co-monomer component consists of one or a combination of at least two co-monomers selected from:
(a) a compound of formula (IV)

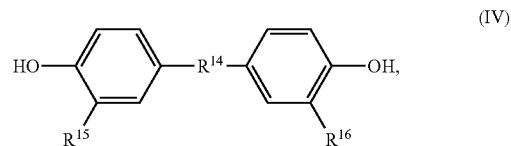

wherein
$R^{14}$ is a difunctional group, and
$R^{15}$ and $R^{16}$ are identical or different independent alkenyl groups with 2 to 6 carbon atoms;
(b) a compound of formula (V)

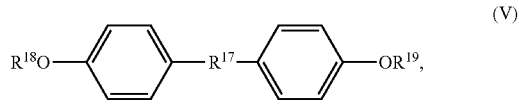

wherein
$R^{17}$ is a difunctional group, and
$R^{18}$ and $R^{19}$ are identical or different independent alkenyl group with 2 to 6 carbon atoms;
(c) a compound of formula (VI)

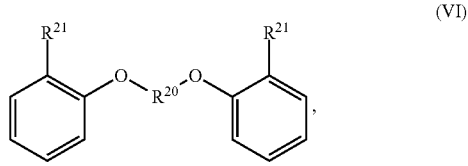

wherein
$R^{20}$ is a difunctional group, and
$R^{21}$ and $R^{22}$ are identical or different and each is independently from the other alkenyl with 2 to 6 carbon atoms;

(d) a compound of formula (VII)

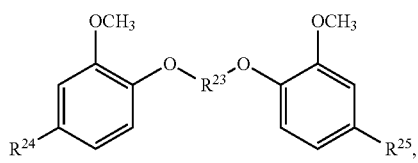
(VII)

wherein
$R^{23}$ is a difunctional group, and
$R^{24}$ and $R^{25}$ are identical or different and each is independently from the other alkenyl with 2 to 6 carbon atoms;

(e) a compound of formula (VIII)

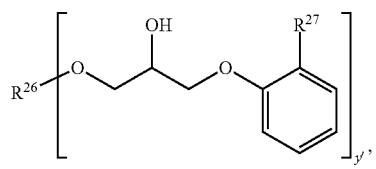
(VIII)

wherein
$R^{26}$ is a y'-functional group, and
$R^{27}$ is an alkenyl group with 2 to 6 carbon atoms, and
y' is an integer $\geq 2$;

(f) a compound of formula (IX)

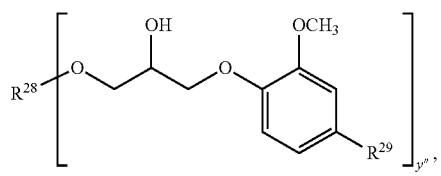
(IX)

wherein
$R^{28}$ is a y''-functional group, and
$R^{29}$ is alkenyl group with 2 to 6 carbon atoms, and
y'' is an integer $\geq 2$.

Preferably residues $R^{14}$ in formula IV and $R^{17}$ in formula V are selected from the following groups:

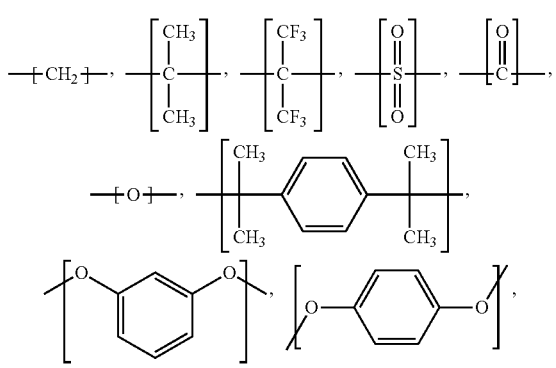

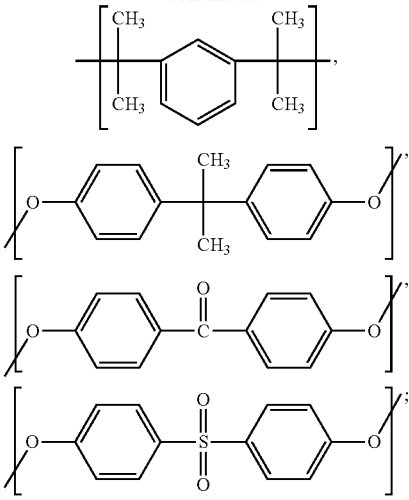

and residues $R^{20}$ in formula VI and $R^{23}$ in formula VII are selected from the following groups

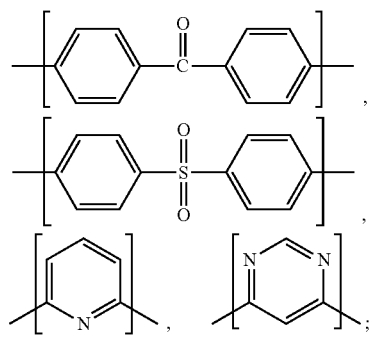

and residues $R^{26}$ in formula VIII and $R^{28}$ in formula IX are difunctional groups selected from the following groups:

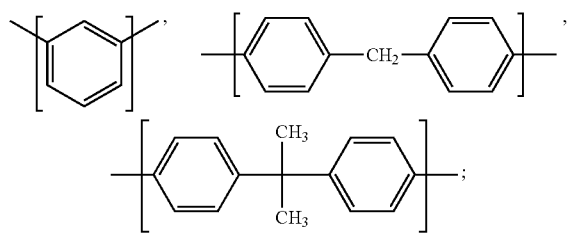

and residues $R^{27}$ in formula VIII and $R^{29}$ in formula IX are 1-propen-1-yl or 2-propen-1-yl groups.

Preferably, the secondary co-monomer component consists of one or a combination of at least two co-monomers selected from:
2,2'-diallylbisphenol-A, bisphenol-A diallyl ether, bis(o-propenylphenoxy)benzophenone, m-aminobenzhydrazide, bisphenol-A dicyanate ester, diallyl phthalate, triallyl isocyanurate, triallyl cyanurate, styrene, divinylbenzene.

Synthesis of Compounds According to Formula (I)

The asymmetrically substituted bis-alkenyl diphenyl ether of the present invention can be prepared by a variety of well known methods from apropriate starting materials such as asymmetrically substituted alkenylphenoxy, alkyl methanone and the appropriate alkylmagnesium halide (Scheme 1) or the appropriate triphenylalkylphosphorane (Scheme 2).

Two methods for the synthesis of asymmetrically substituted bis-alkenyl diphenyl ether are outlined below. Synthetic approach 1 is based on a Grignard reaction utilizing the appropriate asymmetrically substituted alkenylphenoxy alkyl methanone, and the appropriate alkyl-magnesium halide and subsequent dehydration. The second synthetic approach is based on a Wittig reaction of the asymmetrically substituted alkenylphenoxy alkyl methanone with the appropriate triphenylalkylphosphorane (Scheme 2).

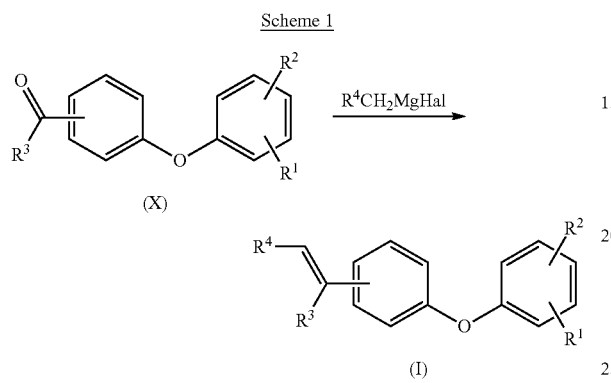

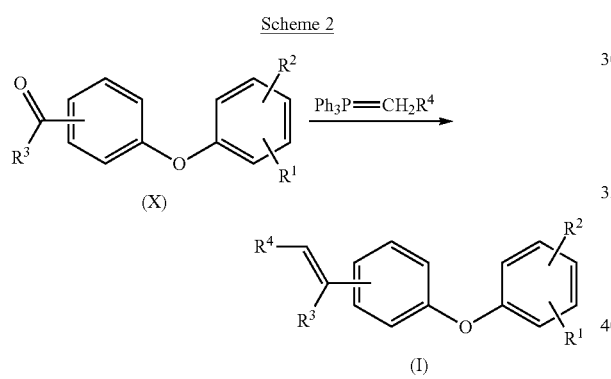

The asymmetrically substituted alkenylphenoxy alkyl methanones (X) can be synthesized from halophenyl alkyl methanone (XI) and an appropriate alkenyl phenol (XII) via a nucleophilic halogen displacement reaction as outlined below (Scheme 3).

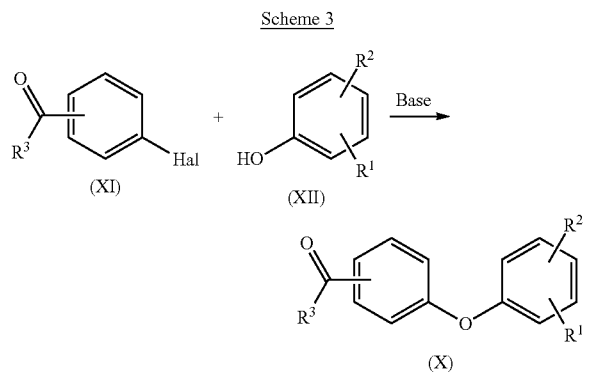

Asymmetrically substituted bis-alkenyl diphenyl ethers of the present invention, in which the alkenyl groups are different in terms of their cis- and trans-configurations, can be prepared from 1,1'-(oxydi-4,1-phenylene)bis-alkanones and the appropriate alkyl magnesium halide or the appropriate triphenylalkylphosphorane (as outlined in Scheme 4).

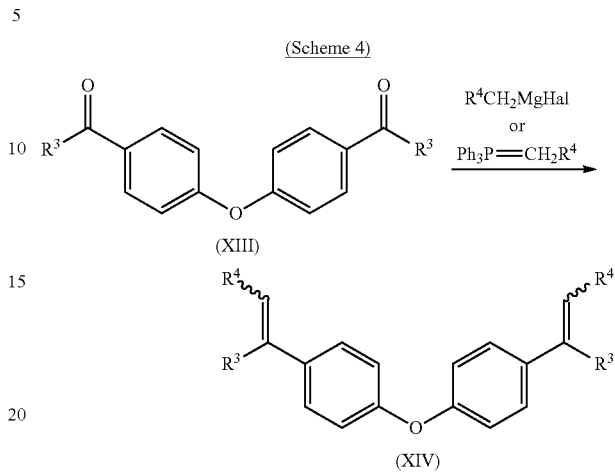

Alternatively, mixed cis/trans bis-alkenyl diphenyl ethers of the present invention can be prepared from 1,1'-(oxydi-4,1-phenylene)bis-alkanones via reduction of the ketone groups followed by the dehydration of a resulting diol (as shown in Scheme 5), similarly to the synthesis of symmetrical bis-(4-vinylphenyl) ether and bis-(4-isopropenylphenyl) ether described in U.S. Pat. U.S. Pat. No. 3,663,625 (Neville, 1972).

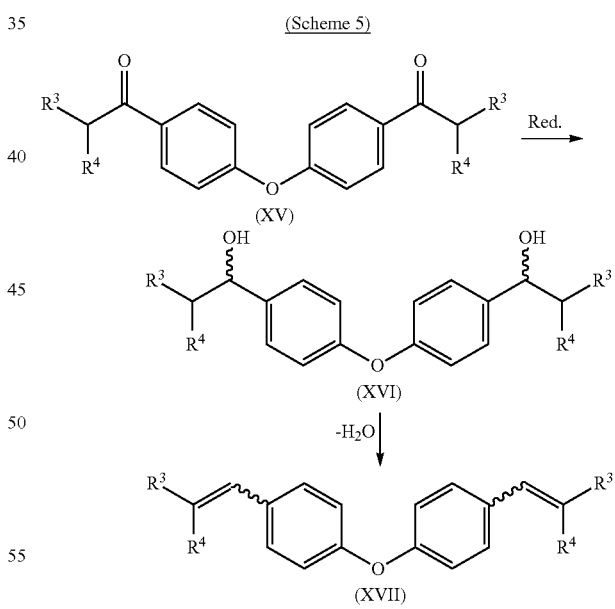

Processes for the Manufacture of Curable Compositions of the Invention

In one aspect, the present invention further relates to processes for the manufacture of curable compositions according to the invention, comprising the step of blending the components of the composition using a powder-, melt-, solvent-assisted or other blending process resulting in solid, low-melting, or tacky curable compositions.

Melt Blending Process

In one aspect, the present invention relates to processes for the manufacture of curable compositions of the invention, comprising the step of:

blending the components of a composition comprising a co-monomer component of the invention and a polyimide component as defined above at a temperature ranging from 70° C. to 250° C. to obtain curable compositions as low melting low viscosity masses (resins).

In the practice of this method, the blending temperatures may be varied over a relatively wide range. In one embodiment, the method is carried out at temperatures from 90° C. to 170° C., preferably from 100° C. to 160° C.

Solution Blending Process

In one aspect, the present invention relates to processes for the manufacture of curable compositions of the invention, comprising the step of:

dissolving the components of a composition comprising a co-monomer component of the invention and a polyimide component as defined above, in a solvent or diluent, and stripping off the solvent or diluent, to obtain a curable composition as a solvent-free, low melting, low viscosity mass (resin).

In one embodiment, the co-monomer component of the invention and the polyimide component as defined above are dissolved in the solvent at elevated temperature.

Suitable solvents and diluents are all customary inert organic solvents. They include but are not limited to ketones such as acetone, methylethylketone, cyclohexanone; glycol ethers such as methyl glycol, methyl glycol acetate, propylene glycol monomethyl ether (methyl proxitol), methyl proxitol acetate, diethylene glycol, and diethylene glycol monomethyl ether; toluene and xylene, preferably in combination with 1,3-dioxolane as a co-solvent.

In a preferred embodiment, the solvent is 1,3-dioxolane or a 1,3-dioxolane-containing solvent.

In one embodiment, the amount of 1,3-dioxolane in the solvent mixture ranges from 20 wt % to 80 wt %, e.g. from 30 wt % to 70 wt % or from 40 wt % to 60 wt %.

In the practice of the processes for the manufacture of the curable composition, i.e. in the melt process and in the solution process, the molar ratio between the unsaturated imide groups and reactive alkenyl groups in the composition ranges from 1.0 to 0.1, e.g. from 1.0 to 0.2, from 1.0 to 0.3, from 1.0 to 0.4, from 1.0 to 0.5, from 1.0 to 0.6, from 1.0 to 0.7 or from 1.0 to 0.8 in order to achieve the desired cure kinetics.

Other Blending Processes

Preparation of the curable compositions of this invention can be carried out without any diluent or solvent in that the components as powders, pastes or liquids are intimately mixed, if necessary at elevated temperature, to obtain a homogeneous blend of the monomers or a prepolymer depending on the duration of the temperature treatment. This process cannot be scaled up to reasonable volumes due to the high reactivity of the BMI/co-monomer mixture. An extruder process may be used to control and set the required melting temperature, to provide the necessary temperature for prepolymerization in the reaction zone and to set the time at temperature by the throughput. The extrudate, after cooling, may be a hot melt product or a solidified melt which can be milled to a resin powder.

Storage Stable Mixtures

For many technical applications of the curable compositions it is advantageous to retard polymerisation by the addition of reaction inhibitors in order to improve processability and storage stability before use. Suitable reaction inhibitors are hydroquinone, 1,4-naphthoquinone and phenothiazine which are used at concentrations between 0.1 wt % and 2.0 wt %, based on the total weight of the composition. It is advantageous to dissolve the inhibitor in one of the components prior to the preparation of the composition.

Compositions Comprising a Secondary Co-Monomer Component

In many cases the curable compositions of the present invention may be processed from the melt. In order to reduce melt viscosity and improve pot life of the resin a secondary co-monomer component may be added, which consists of one or more co-monomers selected from alkenylphenol, alkenylphenyl ether, alkenyl phenol ether, polyamine, aminophenol, aminoacid hydrazide, cyanate ester, diallyl phthalate, triallyl isocyanurate, triallyl cyanurate, styrene, divinylbenzene, wherein the secondary co-monomer component represents between 1 wt % and 30 wt % of the total composition. Of these, allyl-type secondary co-monomer components such as diallylbisphenol-A, bisphenol-A diallylether, diallylphthalate, triallylisocyanurate and triallylcyanurate when added to the curable composition slow down polymerisation kinetics and therefore widen the processing window. Secondary co-monomer components like styrene or divinylbenzene are very effective in concentrations between 10 wt % and 20 wt % but accelerate polymersation kinetics, providing faster curing resins and lowering their polymerisation temperature. Therefore, secondary co-monomer components are an additional tool to modify cure velocity of the curable compositions of the invention. In cases where such secondary co-monomer components are used it is advantageous to first blend the compound (I) with the secondary co-monomer component in the required proportion and then, in a second step, dissolve the polyimide part of the mixture in this blend, if nessecary at elevated temperature.

Compositions Comprising Thermoplastic Toughening Modifier

Curable compositions of the present invention may further include from 0 wt % to about 30 wt %, based on the total weight of the composition, of a thermoplastic polymer such as, for example, a polyaryl ether, a polyaryl sulfone, a polyarylate, a polyamide, a polyaryl ketone, a polyimide, a polyimide-ether, a polyolefin, an ABS resin, a polydiene or diene copolymer or mixtures thereof. Thermoplastics such as polysulfons and phenoxy resins are particularly miscible with the curable compositions of the present invention, and may be used to adjust resin viscosity and control flow during cure. Thermoplastic polymers may also be added to improve the fracture toughness. Thermoplastic polymers can be added to the curable compositions as fine powders, or may be dissoved in either the compound (I) or a secondary co-monomer component.

The curable compositions of the invention can be isolated by customary techniques and processes (cf. e.g. examples section).

Pre-Polymers of Curable Compositions of the Invention and Processes for their Manufacture In one aspect the present invention relates to the use of a curable composition as defined above for the preparation of a prepolymer.

It has been found that the curable compositions of the invention are useful for the preparation of partially crosslinked products (i.e. prepolymers). Prepolymers are prepared by heating curable compositions as defined above to temperatures of 80° C. to 350° C., preferably to 100° C. to 250° C. for a time sufficient to obtain a prepolymer which is still formable upon applying heat and/or pressure. Optionally this is performed in the presence of a cure catalyst or cure stabilizer.

Cure Accelerators

For some applications of the curable compositions of the present invention it is advantageous to accelerate the curing process by adding catalysts, typically in an amount of 0.01 wt % to 5 wt %, preferably in an amount of 0.1 wt % to 2 wt % based on the total weight of the curable composition. Suitable catalysts include ionic and free radical polymerization catalysts. Examples for free radical polymerization catalysts include (a) organic peroxides such as ditertiary butyl peroxide, diamylperoxide and t-butylperbenzoate and (b) azo compounds such as azobisisobutyronitrile. Examples of ionic catalysts are alkali metal compounds, tertiary amines such as triethylamine, dimethylbenzylamine, dimethylaniline, azabicyclooctane, heterocyclic amines such as quinoline, N-methylmorpholine, methylimidazole and phenylimidazole and phosphorous compounds such as triphenylphosphine and quatenary phosphonium halides. The catalysts can be admixed with the components of the curable composition or may be added during the production of the prepolymers either by a powder blending process or by a solvent blending process as described above.

In another aspect the present invention further comprises curable pre-polymers obtainable from curable compositions according to the invention, by a process comprising the step of heating the curable composition to a temperature in the range of 50° C. to 250° C., preferably to 70° C. to 170° C., for a time sufficient to obtain a pre-polymer, which is still formable upon the application of heat and/or pressure.

If the method is carried out in the presence of a solvent, high boiling point polar solvents such as dimethylformamide, dimethylacetamide, N-methylpyrrolidone, and butyrolactone can in principle be used. However, the use of such solvents generally yields prepolymers with high contents of residual solvents.

If the method is carried out in the presence of a solvent, in one embodiment low boiling solvent mixtures containing 1,3-dioxolane may be used. These preferably include, but are not limited to, solvent mixtures of 1,3-dioxolane with ketones such as acetone, methylethylketone, cyclohexanone or glycol ethers such as ethylene glycol ether, propylene glycol ether, butylene glycol ether and their acetates.

Due to the low boiling point of solvent mixtures comprising 1,3-dioxolane and the above-identified solvents, such solvent mixtures are useful for the preparation of solvent free prepolymers. Further, the so obtained prepolymers can be processed to void-free fiber-reinforced composites.

In one embodiment, the solvent mixture comprises up to 50 wt %, preferably up to 40 wt % of ketones such as acetone, methylethylketone, cyclohexanone, or glycol ethers such as ethylene glycol ether, propylene glycol ether, butylene glycol ether, and their acetates based on the total weight of the solvent mixture.

In one embodiment, a solution of the curable composition of the invention comprises from 30 wt % to 70 wt %, preferably from 40 wt % to 60 wt % of solvent, e.g. of 1,3-dioxolane, or solvent mixtures comprising 1,3-dioloxane, and the above-identified solvents. Such concentrations are typically used in industrial dip coating processes.

The prepolymers of the curable composition of the invention can be isolated by generally customary processes, e.g. by evaporation of the solvent if the subsequent use is solvent free.

The prepolymers which are obtained according to the method of the invention are still soluble in selected organic solvents. Further, the prepolymers of the invention are still fusible and formable upon the application of heat and/or pressure.

In another aspect, the present invention relates to a curable prepolymer obtainable according to a method as described above.

Crosslinked Polymers of the Curable Compositions of the Invention and Processes for their Manufacture In one aspect, the invention relates to the use of a curable composition as defined above or of a prepolymer as defined above for the preparation of a crosslinked polymer.

It has been found that the curable compositions and curable prepolymers of the invention are useful for the preparation of crosslinked polymers.

In one aspect, the invention relates to a method for the preparation of a crosslinked polymer comprising the step of:
heating a curable composition as defined above or a curable prepolymer as defined above to a temperature ranging from 70° C. to 280° C. for a time sufficient to complete cure.

In the practice of this method, the reaction temperatures may be varied over a relatively wide range. In one embodiment, the method is carried out at temperatures from 80° C. to 270° C., more preferably from 90° C. to 260° C., most preferably from 100° C. to 250° C.

In another aspect the present invention further comprises crosslinked polymers obtainable from the curable compositions according to the invention by a process comprising the step of heating the curable composition to a temperature in the range of 70° C. to 280° C. for a time sufficient to obtain a polymer.

The conversion may take place with simultaneous shaping under pressure to obtain mouldings, laminates, adhesive bonds, and foams.

For these applications, it is possible to admix the curable composition with additives such as fillers, pigments, colorants, and flame retardants. Suitable fillers are glass- or carbon fibers, graphite, quartz, metal powders, and metal oxides. Mould release agents such as silicone oil, waxes, Zn and K-stearates may also be added.

In another aspect, the present invention relates to mouldings, laminates, adhesive bonds, and foams obtainable by processing of the curable composition and curable prepolymers of the invention.

Composite Materials of the Invention and Processes for their Manufacture

It has been found that curable compositions and prepolymers of the invention are useful for the preparation of composite materials.

Mixtures Containing Particulate Fillers

The curable compositions of the present invention can be processed by known methods of the powder moulding industry for producing mouldings, with curing taking place with simultaneous shaping under pressure. For these applications the curable compositions are admixed with additives such as fillers, colorants and flame retardants. Ideal fillers for example are short glass fibers, short carbon fibers or aramid fibers, paticulate fillers such as quartz, silica, ceramics, metal powders and carbon powder. Depending on the technical application of the moulded article two or more different fillers may be used at the same time.

Applications

One of the preferred uses of the curable compositions of the present invention is as binders for fiber composites. For this application fibers such as glass, carbon or aramid in the form of rovings, fabrics, short fiber mats, or felts are impregnated with the curable composition, employing a solution of the said curable composition to impregnate said reinforcements. After drying off the solvent a prepreg is left, which in the second phase may be cured at a temperature between 180° C. and 350° C., optionally under pressure.

Melt Prepregs

A preferred application oft the curable compositions of the present invention is as hot-melt resins for fiber-reinforced composites. In order to obtain such fiber-reinforced composites the curable compositions are processed as hot melts to a resin film on a carrier foil, subsequently fibers, in the form of rovings or fabrics, are pressed into the molten resin film to form a prepreg. For this process curable compositions, which have a low viscosity at low temperature are advantageous in order to provide adequate impregnation of fiber rovings or fabric.

Laminates

One of the preferred applications of the curable compositions of the present invention is as resins for fiber laminates. Prepregs manufactured by either the solvent/solution- or the hot-melt process from glass-, carbon- or aramid fibers, in the form of fabriques or rovings, are stacked to provide a prepreg laminate, which subsequently is cured under pressure or in a vacuum bag at a temperature between 150° C. and 280° C. preferably between 170° C. and 260° C.

In one aspect, thus, the invention relates to a method for the preparation of a composite material comprising the steps of:

applying or blending a curable composition in form of a low-viscosity-melt stable resin obtainable according to the method as defined above, or a prepolymer as defined above, onto or with a fibrous or particulate reinforcement (filler); and subsequent curing.

In one embodiment, the curable composition or the prepolymer as defined above is applied onto or blended with a fibrous or particulate reinforcement (filler) with the use of standard processing techniques, e.g with the use of the hot melt or solution-based prepregging, resin transfer moulding (RTM), resin infusion moulding (RIM), filament winding (FW) or compounding techniques.

Curing may be carried out at temperatures ranging from 70° C. to 280° C., preferably at temperatures ranging from 80° C. to 270° C., more preferably at temperatures ranging from 90° C. to 260° C., most preferably at temperatures ranging from 100° C. to 250° C. for a time sufficient to complete cure.

In another aspect the present invention further comprises processes for the manufacture of composite materials comprising the steps of combining a curable composition according to the invention or a curable pre-polymer according to the invention, with a fibrous or particulate reinforcement, and curing the resultant product.

In one embodiment, the composite material is a fiber-reinforced composite.

In one embodiment, the composite material is a particulate-filled composite.

In one aspect, the present invention relates to a method for the preparation of a composite material comprising the steps of:
(a) preparing a curable composition or a prepolymer thereof as defined above,
(b) applying a curable composition or a prepolymer thereof as defined above onto a fibrous reinforcement or blending with a particulate filler,
(c) curing the curable composition or prepolymer thereof as defined above at a temperature ranging from 70° C. to 280° C. for a time sufficient to complete cure, and
(d) simultaneously applying pressure to obtain the composite material.

Process step c) may be carried out at temperatures ranging from 70° C. to 280° C., preferably at temperatures ranging from 80° C. to 270° C., more preferably at temperatures ranging from 90° C. to 260° C., most preferably at temperatures ranging from 100° C. to 250° C. for a time sufficient to complete cure.

In the practice of process step c) the conversion of the curable compositions or prepolymers of the invention into the crosslinked (cured) polymer may be carried out, in the presence of a curing catalyst as defined above.

In the practice of process step d) shaping under pressure is performed to obtain the composites of the invention. Process steps c) and d) are carried out simultaneously.

A preferred application of the curable compositions of the invention is resins for fiber-reinforced composites. In order to obtain such fiber composites the curable compositions of the invention are processed as hot melts to resin film on a carrier foil, which is subsequently used to prepare prepolymers by pressing fibers in the form of rovings or fabrics into the resin film. For this process curable compositions, which have a low viscosity at low temperature are advantageous in order to provide adequate impregnation of fiber rowings or fabric.

In one aspect the present invention comprises composite materials obtainable by a process according to the invention.

Definitions

As used herein, including the accompanying claims, the terms, which are collectively used, have the following meanings.

As used herein, the term "curable" means that an original compound(s) or mixture material(s) can be transformed into a solid, substantially non-flowing material by means of chemical reaction, crosslinking, radiation crosslinking or the like.

As used herein, the term "mixture" means a physical or mechanical aggregation or a combination of two or more individual, chemically distinct compounds that are not chemically united.

As used herein, the term "polyimide component" means one polyimide or a mixture of two or more polyimides, preferably one polyimide or a mixture of two to four polyimides.

As used herein, the term "co-monomer" means a compound that can undergo polymerization or copolymerization, thereby contributing constitutional units to the essential structure of a polymer.

As used herein, the term "co-monomer component" means one co-monomer or a mixture of two or more co-monomers, preferably one co-monomer or a mixture of two to four co-monomers.

As used herein, the term "alkenylphenol" means organic compounds comprising at least one alkenyl-substituted phenol group. The term "alkenylphenol" comprises alkenylphenols, wherein two phenol groups are bridged via a difunctional group, e.g. alkenylbisphenols. Examples include 2,2'-diallyl-bisphenol A.

As used herein, the term "alkenylphenyl ether" means organic compounds comprising at least one alkenyloxyphenyl group, i.e. an ether group wherein the ether oxygen atom is connected on one hand to an alkenyl residue and on the other hand to a phenyl residue. The term "alkenylphenyl ether" comprises alkenylphenyl ethers, wherein two phenyl groups are bridged by a difunctional group, e.g. alkenylbisphenol ether. Examples include diallyl ether of bisphenol A.

As used herein, the term "alkenylphenol ether" means organic compounds comprising at least one alkenylphenoxy group, e.g. an ether group wherein the ether oxygen atom is connected on one hand to an alkenylphenyl group and on the other hand to a an alkyl or an aryl group. The term "alkenylphenol ether" comprises organic compounds, wherein two alkenylphenoxy groups are bridged by a difunctional group, e.g. by an aromatic group such as a benzophenone group. Examples include bis-(o-propenylphenoxy)benzophenone.

As used herein, the term "polyamine" means an organic compound having two or more primary amino groups —$NH_2$. Examples include, but are not limited to 4,4'-diaminodiphenylmethane, 4,4'-diaminodiphenylsulfone, 3,3'-diaminodiphenylsulfone, diaminodiphenylindane, m-phenylenediamine, p-phenylenediamine, 2,4-diaminotoluene, 2,6-diaminotoluene, m-xylylenediamine and aliphatic diamines such as ethylenediamine, hexamethylenediamine, trimethylhexamethylenediamine, 1,12-diaminododecane.

As used herein, the term "aminophenol" means amino-substituted phenols. Examples include m-aminophenol and p-aminophenol.

As used herein, the term "amino acid hydrazides" means any hydrazides of amino acids. Examples include m-aminobenzhydrazide and p-aminobenzhydrazide.

As used herein, the term "cyanate ester" means a bisphenol or polyphenol, e.g. novolac, derivative, in which the hydrogen atom of the phenolic OH group is substituted by a cyano-group, resulting in an —OCN group. Examples include bisphenol A dicyanate ester, commercially available as, e.g. Primaset BADCy from Lonza or AroCy B-10 from Huntsman, as well as other Primaset or AroCy types, e.g. bis(3,5-dimethyl-4-cyanatophenyl)methane (AroCy M-10), 1,1-bis(4-cyanatophenyl)ethane (AroCy L-10), 2,2-bis(4-cyanatophenyl)-1,1,1,3,3,3-hexafluoropropane (AroCy F-10), 1,3-bis(1-(4-cyanatophenyl)-1-methylethylidene)benzene (AroCy XU-366), di(4-cyanatophenyl)thioether (AroCy RDX-80371; AroCy T-10), bis(4-cyanatophenyl)dichloromethylidenemethane (AroCy RD98-228), bis(4-cyanatophenyl)octahydro-4,7-methanoindene (AroCy XU-71787.02L), as well as bis(4-cyanatophenyl)methane, bis(3-methyl-4-cyanatophenyl)methane, bis(3-ethyl-4-cyanatophenyl)methane, di(4-cyanatophenyl)ether, 4,4-dicyanatobiphenyl, 1,4-bis(1-(4-cyanatophenyl)-1-methylethylidene)benzene, resorcinol dicyanate. A preferred example is bisphenol A dicyanate ester.

Any bond intersected by a bracket indicates a bond that connects the moiety within the bracket to other moieties of the same compound. For example, in the group shown below the two bonds of the ethenyl group intersected by the bracket on the right side connect this moiety to other moieties of the compound containing this ethenyl group

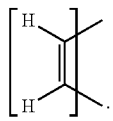

As used herein, the term "halogen" means a fluorine, chlorine, bromine or iodine atom, preferably a fluorine or chlorine atom, more preferably a fluorine atom.

As used herein, "alkyl" means a straight-chain or branched alkyl group. The term "alkyl with n to m carbon atoms" means an alkyl group with n to m carbon atoms. If not denoted otherwise, "alkyl" means an alkyl with 1 to 6 carbon atoms. In the context of the present invention, preferred alkyl groups are straight-chain or branched alkyl groups with 1 to 4 carbon atoms. Examples of straight-chain and branched alkyl groups include, but are not limited to methyl, ethyl, propyl, isopropyl, butyl, isobutyl, tert.-butyl, the isomeric pentyls, the isomeric hexyls, preferably methyl and ethyl and most preferred methyl.

As used herein, "alkylene" means a difunctional alkyl group. The term "alkylene with n to m carbon atoms" means an alkylene group with n to m carbon atoms. If not denoted otherwise, "alkylene" means an alkylene with 1 to 12 carbon atoms. In the context of the present invention, preferred alkylene groups are alkylene groups with 1 to 9 carbon atoms, more preferably from 1 to 6 carbon atoms. Examples include, but are not limited to methylene, ethylene, propylene, butylene, hexamethylene and 2,2,4-trimethylhexamethylene. Particularly preferred is 2,2,4-trimethylhexamethylene.

As used herein, "alkenylene" means a difunctional alkenyl group. The term "alkenylene with n to m carbon atoms" means an alkenylene group with n to m carbon atoms. If not denoted otherwise, "alkenylene" means an alkenylene with 2 to 12 carbon atoms. In the context of the present invention, preferred alkenylene groups are alkenylene groups with 2 to 10 carbon atoms, more preferably from 2 to 6 carbon atoms. Examples include, but are not limited to ethenylene, propenylene, and butenylene. Particularly preferred is ethenylene.

As used herein, "alkoxy" means a straight-chain or branched alkyl group, which is bonded to the compound via an oxygen atom (—O—). The term "alkoxy with n to m carbon atoms" means an alkoxy with n to m carbon atoms. If not denoted otherwise, "alkoxy" means a straight-chain or branched alkyl group with 1 to 6 carbon atoms. In the context of the present invention, preferred alkoxy groups are straight-chain or branched alkoxy groups with 1 to 4 carbon atoms.

As used herein, "alkenyl" means a straight-chain or branched hydrocarbon group comprising a carbon-carbon double bond. The term "alkenyl with n to m carbon atoms" means an alkenyl with n to m carbon atoms. If not denoted otherwise, "alkenyl" means a straight-chain or branched hydrocarbon group comprising a carbon-carbon double bond in any desired position and 2 to 10 carbon atoms. In the context of the present invention, preferred alkenyl groups comprise a carbon-carbon double bond in any desired position and 2 to 6, more preferably 2 to 4 carbon atoms. Examples of alkenyl groups include, but are not limited to ethenyl, 1-propenyl, 2-propenyl, isopropenyl, 1-butenyl, 2-butenyl, 3-butenyl and isobutenyl. Preferred examples are 1-propenyl and 2-propenyl.

As used herein the term "monocarbocyclic group" means a "monocarbocyclic aliphatic group" or a "monocarbocyclic aromatic group".

As used herein the term "dicarbocyclic group" means a a "dicarbocyclic aliphatic group" or a "dicarbocyclic aromatic group" group.

As used herein the term "monocarbocyclic aliphatic group" means a cycloalkylene group.

As used herein, "cycloalkyl" means a monofunctional carbocyclic saturated ring system. The term "cycloalkyl with n to m carbon atoms" means a cycloalkyl with n to m carbon atoms. If not denoted otherwise, "cycloalkyl" means a cycloalkyl group with 5 to 6 carbon atoms. Examples of cycloalkyl groups include, but are not limited to cyclopropanyl, cyclobutanyl, cyclopentanyl, cyclohexanyl, cycloheptanyl or cyclooctanyl, preferably cyclopentanyl and cyclohexanyl.

As used herein, "cycloalkylene" means a difunctional carbocyclic saturated ring system. The term "cycloalkylene with n to m carbon atoms" means a cycloalkylene with n to m carbon atoms. If not denoted otherwise, "cycloalkylene" means a cycloalkylene group with 3 to 8 carbon atoms. In the context of the present invention preferred cycloalkylene groups are cycloalkylene groups with 5 to 7, more preferably 5 or 6 carbon atoms. Examples include, but are not limited to cyclopropylene, cyclobutylene, cyclopentylene, cyclohexylene, cycloheptylene or cyclooctylene, preferably cyclopentylene and cyclohexylene.

As used herein, "dicarbocyclic aliphatic group" means a difunctional bicyclic condensed, bridged or fused saturated ring system. If not denoted otherwise, "dicarbocyclic aliphatic group" means a difunctional bicyclic condensed, bridged or fused saturated ring system with 9 to 20 carbon atoms. Examples include, but are not limited to decalinyl, hydrindanyl and norbornyl.

As used herein, the term "mono- or dicarbocyclic aromatic group" means a difunctional mono- or dicyclic aromatic system, preferably with 6 to 12 carbon atoms, preferably a monocyclic aromatic system. Examples include, but are not limited to, toluene, phenylene, naphthylene, tetrahydronaphthylene, indenylene, indanylene, pentalenylene, fluorenylene and the like, preferably toluene, phenylene or indanylene.

As used herein, the term "aryl" means a monofunctional mono- or dicyclic aromatic system, preferably with 6 to 12 carbon atoms, preferably a monocyclic aromatic system. Examples include, but are not limited to, toluyl, phenyl, naphthyl, tetrahydronaphthyl, indenyl, indanyl, pentalenyl, fluorenyl and the like, preferably toluyl, phenyl or indanyl.

As used herein, the term "heterocyclic group" means a "heterocyclic aliphatic group" or a "heterocyclic aromatic group"

As used herein, the term "heterocyclic aliphatic group" means a difunctional saturated ring system which, in addition to carbon atoms, comprises one, two or three atoms selected from nitrogen, oxygen and/or sulfur. Preferred heterocyclic aliphatic groups are those containing 3 to 5 carbon atoms and one nitrogen, oxygen or sulfur atom.

As used herein, the term "heterocyclic aromatic group" means a monocyclic aromatic 5- or 6-membered ring, which comprises one, two or three atoms selected from nitrogen, oxygen and/or sulfur, or a bicyclic aromatic group comprising two 5- or 6-membered rings, in which one or both rings can contain one, two or three atoms selected from nitrogen, oxygen or sulfur. Examples include, but are not limited to pyridyl, pyrazinyl, pyrimidinyl, pyridazinyl, oxazolyl, oxydiazolyl, isoxazolyl, thiadiazolyl, tetrazolyl, pyrazolyl, imidazolyl, thiazolyl, thienyl, quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl, indazolyl.

As used herein the term "bridged multicyclic group" means a group consisting of at least two groups selected from monocarbocyclic aromatic groups, dicarbocyclic aromatic groups, cycloalkylene groups; wherein these groups are linked to each other by direct carbon-carbon bonds or by divalent groups.

Preferred divalent groups are oxy-group, thio-group, alkylene-group with 1 to 3 carbon atoms, sulfone-group, methanone-group, and the following groups:

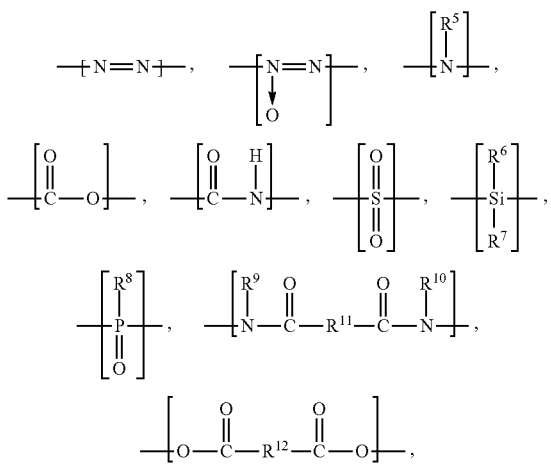

wherein $R^5$, $R^6$, $R^7$, $R^8$, $R^9$, $R^{10}$ are independently an alkyl group with 1 to 6 carbon atoms; and $R^{11}$ and $R^{12}$ are independently an alkylene group with 1 to 6 carbon atoms;

In one embodiment the term "bridged multicyclic group" means a group consisting of two monocarbocyclic aliphatic groups, which are linked to each other by a direct carbon-carbon bond or by a divalent group such as oxy-group, thio-group, alkylene-group with 1 to 3 carbon atoms, sulfone-group, methanone-group, or one of the following groups:

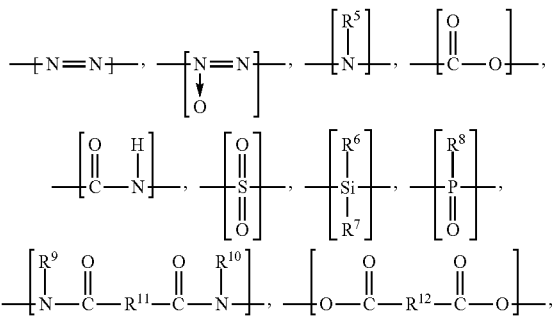

wherein $R^5$, $R^6$, $R^7$, $R^8$, $R^9$, $R^{10}$ are independently an alkyl group with 1 to 6 carbon atoms; and $R^{11}$ and $R^{12}$ are independently an alkylene group with 1 to 6 carbon atoms.

In one embodiment the term "bridged multicyclic group" means a group consisting of two cyclohexylene groups, which are linked to each other by a direct carbon-carbon bond or by a divalent group such as oxy-group, thio-group, alkylene-group with 1 to 3 carbon atoms, sulfone-group, methanone-group.

In one embodiment the term "bridged multicyclic group" means a group consisting of two monocarbocyclic aromatic groups, which are linked to each other by a direct carbon-carbon bond or by a divalent group such as oxy-group, thio-group, alkylene-group with 1 to 3 carbon atoms, sulfone-group, methanone-group, or one of the following groups:

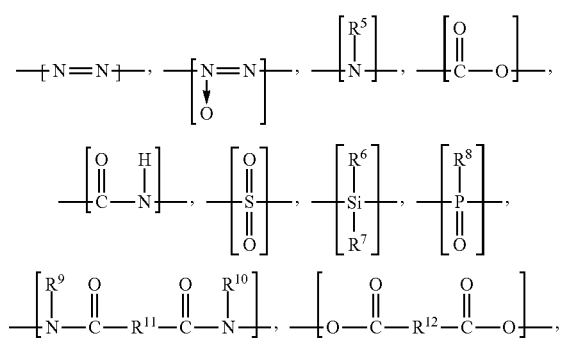

wherein $R^5$, $R^6$, $R^7$, $R^8$, $R^9$, $R^{10}$ are independently an alkyl group with 1 to 6 carbon atoms; and $R^{11}$ and $R^{12}$ are independently an alkylene group with 1 to 6 carbon atoms.

In one embodiment the term "bridged multicyclic group" means a group consisting of two phenylene groups, which are linked to each other by a direct carbon-carbon bond or by a divalent group such as oxy-group, thio-group, alkylene-group with 1 to 3 carbon atoms, sulfone-group, methanone-group.

As used herein, the addition of the terms "unsubstituted" or "substituted" means that the respective groups are unsubstituted or carry from 1 to 4 substituents selected from alkyl, alkoxy and halogen. Preferred substituents are methyl or ethyl.

As used herein, the terms "x-functional group", "y-functional group", "y'-functional group" and "y"-functional group" respectively, denote a group, which is bonded to the remainder of the compound via x, y, y', or y" bond(s), respectively. Preferably, the "x-functional group", "y-functional group", "y'-functional group" and "y"-functional group" is a difunctional group, i.e. x, y, y"and y" are preferably 2.

As used herein, the term "difunctional group" means a group, which is bonded to the remainder of the compound-svia two bonds. Difunctional groups include but are not limited to, difunctional aliphatic groups and difunctional aromatic groups. Difunctional aliphatic groups include but are not limited to the following groups:

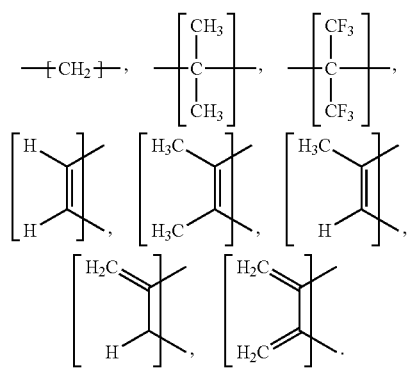

Difunctional aromatic groups include but are not limited to the following groups:

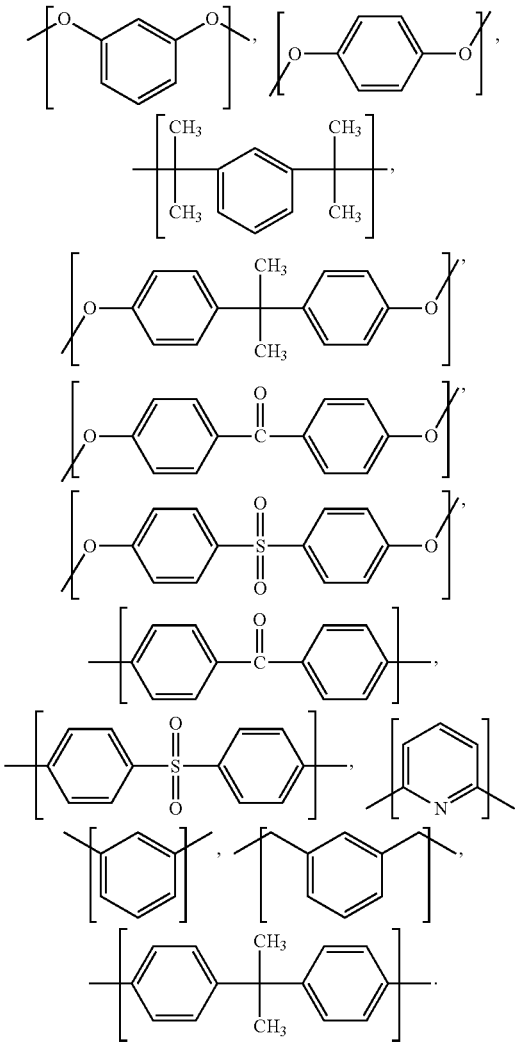

Difunctional aromatic groups include but are not limited to the following groups:

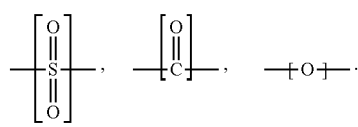

As used herein, the term "Glass transition temperature" or "Tg" means the temperature of reversible transition of an amorphous solid, e.g. polymer, between high elastic state and vitreous (glassy) state, when the polymer becomes brittle on cooling, or soft on heating. More specifically, it defines a pseudo second order phase transition, in which a supercooled melt yields, on cooling, a glassy structure and properties similar to those of crystalline materials, e.g. of an isotropic solid material.

As used herein, the term "asymmetrically substituted bis-alkenyl diphenyl ethers" refers to diphenyl ethers according to formula (I), i.e. phenyl residues bound to each other via an oxygen (ether) bridge, bearing one alkenyl-substituent at each of the two phenyl rings and optionally, further, one alkoxy-substituent on one of the two phenyl rings, wherein these diphenyl ethers meet at least one of the following requirements (1) to (4):
(1) the alkenyl-substituents are different, and their regiopositions at corresponding phenyl rings are either the same (i.e. ortho,ortho'-, meta,meta'-, or para,para'-) or different (i.e. ortho,meta'-, orto,para'-, meta,ortho'-, meta,para'-, para,ortho'-, or para,meta'-);
(2) the alkenyl-substituents are the same, and their regiopositions at corresponding phenyl rings are different (i.e. ortho,meta'-, orto,para'-, or meta,para'-);
(3) the alkenyl-substituents are the same, and their regiopositions at corresponding phenyl rings are also the same (i.e. ortho,ortho'-, meta,meta'-, or para,para'-), but configurations of their double bonds are different (i.e. cis- and trans-),
(4) the alkenyl-substituents are the same, their regiopositions at corresponding phenyl rings are the same (i.e. ortho,ortho'-, meta,meta'-, or para,para'-), and configurations of their double bonds are also the same (i.e. cis- and trans-), but one of the two phenyl rings bears an alkoxy-substituent.

In accordance with the above definition and as used herein, the term "symmetrically substituted bis-alkenyl diphenyl ethers" refers to diphenyl ethers according to formula (I), i.e. phenyl residues bound to each other via an oxygen (ether) bridge, bearing one alkenyl-substituent at each of the two phenyl rings, wherein the alkenyl-substituents, their regiopositions at corresponding phenyl rings, and configurations of double bonds at the alkenyl-substituents are the same and none of the two phenyl rings bears an alkoxy-substituent.

EXAMPLES

The following examples are intended to illustrate but not to limit the present invention.

Examples

A. Synthesis of Alkenylphenoxy Substituted Acetophenone Precursors

Example 1

Synthesis of 4-[2-(prop-1-en-1-yl)phenoxy]-acetophenone

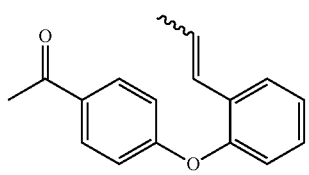

2-Allylphenol (134.18 g), 4-fluoroacetophenone (138.14 g), dry potassium carbonate (138 g), and 250 ml of dry N-methylpyrrolidone were charged in a 3-necked 1.5 l flask, fitted with a stirrer, reflux condensor, and thermometer, and the mixture was heated for 17 hours at 155° C. under nitrogen. Subsequently, the mixture was cooled down to 70° C. and 400 ml of toluene and 500 ml of water were added and vigorously stirred at 70° C. for 30 mins. The phases were separated, the aqueous phase discarded, and the organic phase was washed three times with each 200 ml of a 10% sodium hydroxide solution at 50° C. To the organic phase were added 250 ml of water and the pH was adjusted to 4.5 by the addition of diluted hydrochloric acid. The aqueous phase was separated and discarded, and the organic phase was filtered through Celite® as a filter aid over basic aluminum oxide. Subsequently the solvent was distilled off by use of a rotary evaporator and, finally, the residue was degassed at 130° C. under reduced pressure, leaving the product as a brown melt. Yield: 95.1%. Purity (HPLC): 95.7% (220 nm), 96.7% (254 nm).

Example 2

Synthesis of 4-[2-methoxy-4-(prop-1-en-1-yl)phenoxy]-acetophenone

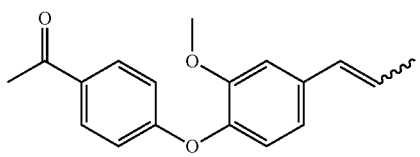

In a similar manner to that described in example 1, eugenol was used as a starting material to synthesize 4-[2-methoxy-4-(prop-1-en-1-yl)phenoxy]-acetophenone. Yield: 96.2%. Purity (HPLC): 88.2% (220 nm), 87.9% (254 nm).

Example 3

Synthesis of 4-[2-ethoxy-5-(prop-1-en-1-yl)phenoxy]-acetophenone

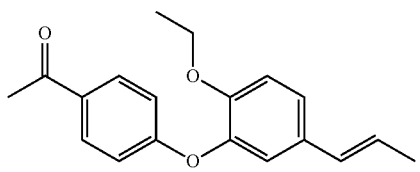 [SMILES: C/C=C/c1ccc(OCC)c(Oc2ccc(C(C)=O)cc2)c1]

In a similar manner to that discribed in example 1, vanitrope was used as a starting material to synthesize 4-[2-ethoxy-5-(prop-1-en-1-yl)phenoxy]-acetophenone. Yield: 94.7%. Purity (HPLC): 97.4% (220 nm), 97.6% (254 nm).

B. Synthesis of Asymmetrically Substituted Bis-Alkenyl Diphenyl Ethers

General procedure for the synthesis of asymmetrically substituted bis-alkenyl diphenyl ethers 0.37 mole of alkyl-triphenylphosphonium bromide and 310 ml of dry tetrahydrofuran were charged into a 3-necked glass reactor, equipped with a stirrer, reflux condensor and thermometer, and cooled down to 3° C. 0.37 mole of potassium tert-butoxide were added to the stirred mixture within 10 min. 0.31 mole of the appropriate propenylphenoxy-acetophenone (prepared according to examples 1 through 3), dissolved in 140 ml of dry tetrahydrofurane, were added within 60 min at, while maintaining temperature between 0° C. and 8° C. Subsequently, the mixture was stirred for additional 60 mins at 5° C. and 60 mins at room temperature. Then, 110 ml of water were added and the mixture was stirred for 10 mins. Tetrahydrofurane was stripped off at a temperature of max. 50° C. under reduced pressure (100 mbar). 300 ml of petroleum ether (80/110) were then added to the residue, and the mixture was stirred for 10 mins at 50° C. Subsequently, 200 ml of water were added and the mixture stirred for 20 mins at room temperature. The precipitated triphenylphosphine oxide (TPO) was filtered off, phases of the filtrate were separated, and the organic phase was washed with water until pH 6 was reached. Additional TPO, which precipitated, was filtered off, the solution was dried over anhydrous CaCl2 and filtered through Celite®. The solvent was stripped off by use of a rotary evaporator, and the residue finally was degassed under reduced pressure at 130° C. for 20 min. The residue was characterized by use of HPLC analysis at 220 and 254 nm.

Example 4

Synthesis of 4-isopropenyl-2'-(1-propen-1-yl)-diphenylether

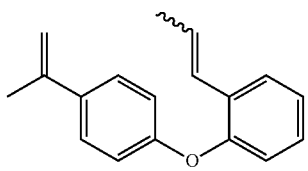

4-[2-(Prop-1-en-1-yl)phenoxy]-acetophenone synthesized according to example 1 was used as a starting material. Yield: 86.4% (brown oil). Purity (HPLC): 99.1% (220 nm), 99.4% (254 nm). The product contained <0.1% of TPO and no starting ketone.

Example 5

Synthesis of 4-isobutenyl-2'-(1-propenyl)-diphenylether

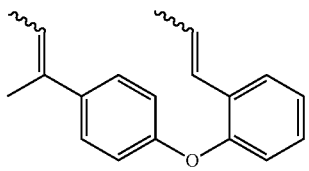

4-[2-(Prop-1-en-1-yl)phenoxy]-acetophenone synthesized according to example 1 was used as a starting material. Yield: 97.3% (brown oil). Purity (HPLC): 94.7% (220 nm), 98.6% (254 nm). The product contained <0.1% of TPO and no starting ketone.

Example 6

Synthesis of 4-isohexenyl-2'-(1-propenyl)-diphenylether

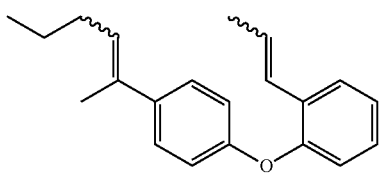

4-[2-(Prop-1-en-1-yl)phenoxy]-acetophenone synthesized according to example 1 was used as a starting material. Yield: 76.9% (brown oil). Purity (HPLC): 96.9% (220 nm), 97.4% (254 nm). The product contained 0.15% of TPO and no starting ketone.

Example 7

Synthesis of 4-isobutenyl-2'-methoxy-4'-(1-propenyl)-diphenylether

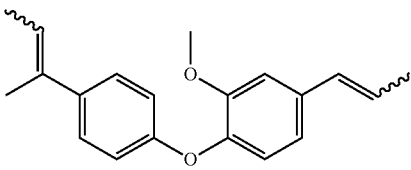

4-[2-Methoxy-4-(prop-1-en-1-yl)phenoxy]-acetophenone synthesized according to example 2 was used as a starting material. Yield: 90.6% (brown oil). Purity (HPLC): 86.2% (220 nm), 97.2% (254 nm). The product contained 0.3% of TPO and no starting ketone.

Example 8

Synthesis of 4-isohexenyl-2'-methoxy-4'-(1-propenyl)-diphenylether

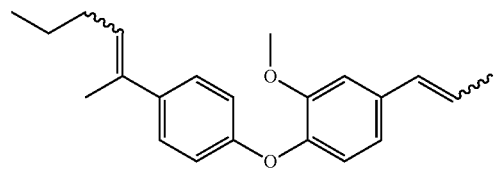

4-[2-Methoxy-4-(prop-1-en-1-yl)phenoxy]-acetophenone synthesized according to example 2 was used as a starting material. Yield: 104.5% as is (brown oil). Purity (HPLC): 85.5% (220 nm), 95.0% (254 nm). The product contained 0.3% of TPO and no starting ketone.

Example 9

Synthesis of 4-isobutenyl-2'-ethoxy-5'-(1-propenyl)-diphenylether

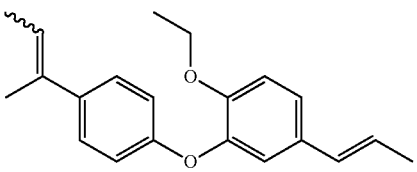

4-[2-Ethoxy-5-(prop-1-en-1-yl)phenoxy]-acetophenone synthesized according to example 3 was used as a starting material. Yield: 94% (brown oil). Purity (HPLC): 93.0% (220 nm), 98.0% (254 nm). The product contained 0.1% TPO and no starting ketone.

Viscosities of asymmetrically substituted bis-alkenyl diphenyl ethers of formula (I), prepared in examples 4 through 9, are compiled in Table 1.

TABLE 1

Viscosities of asymmetrically substituted bis-alkenyl diphenyl ethers.

| Example No. | Asymmetrically substituted bis-alkenyl diphenyl ethers | Viscosity (mPa · s) at 23° C. | at 50° C. |
|---|---|---|---|
| 4 | 4-Isopropenyl-2'-(prop-1-en-1-yl)-diphenyl ether | 28.7 | 9.33 |
| 5 | 4-(1-Methylprop-1-en-1-yl)-2'-(prop-1-en-1-yl)-diphenyl ether | 47.9 | 12.8 |
| 6 | 4-(1-Methylpent-1-en-1-yl)-2'-(prop-1-en-1-yl)-diphenyl ether | 59.1 | 14.9 |
| 7 | 4-(1-Methylprop-1-en-1-yl)-2'-methoxy-4'-(prop-1-en-1-yl)-diphenyl ether | 2972 | 129 |
| 8 | 4-(1-Methylpent-1-en-1-yl)-2'-methoxy-4'-(prop-1-en-1-yl)-diphenyl ether | 1965 | 134 |
| 9 | 4-(1-Methylprop-1-en-1-yl)-2'-ethoxy-5'-(prop-1-en-1-yl)-diphenyl ether | 252 | 32.6 |

Table 2 provides melting points of symmetrically substituted bis-alkenyl diphenyl ethers for comparison purposes.

TABLE 2

Melting points of symmetrically substituted bis-alkenyl diphenyl ethers.

| Comparative Example | Symmetric bis-alkenyl-diphenyl ethers | Formula | CAS No. | Melting point, ° C. |
|---|---|---|---|---|
| Lit. [1,2] | Bis(4-isopropenyl)-phenyl ether | 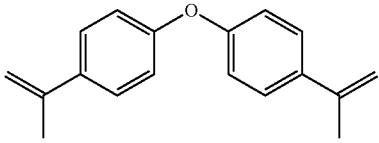 [SMILES: C=C(C)c1ccc(Oc2ccc(C(=C)C)cc2)cc1] | 22583-02-4 | 107 |
| Lit. [3] | Bis[4-(prop-1-en-1-yl)]phenyl ether | 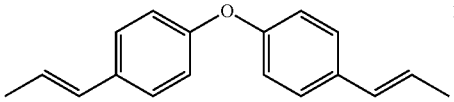 [SMILES: C/C=C/c1ccc(Oc2ccc(/C=C/C)cc2)cc1] | 175887-07-7 | 117-119 |
| Lit. [4] | Bis(4-vinylphenyl) ether | 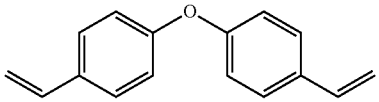 [SMILES: C=Cc1ccc(Oc2ccc(C=C)cc2)cc1] | 7659-54-3 | 89-90 |

[1] R.G. Neville: Bis[1-alkyl (or aryl) vinyl]-p-phenylene oxide monomers // U.S. Pat. US 3663625 A, 16 May 1972 (Bechtel International Corp.).
[2] J.E. Harris, A. Berger, V.M Chopdekar, M. Matzner, J. Spanswick: Amide and/or imide containing polymers and monomers for the preparation thereof // U.S. Pat US 4713438 A, 15 Dec 1987 (Amoco Corp., USA).
[3] J.T. Aplin, N.L. Bauld; Mechanistic distinctions between cation radical and carbocation propagated polymerization // J. Org. Chem., 1998, Vol. 63, No. 8, 2586-2590.
[4] R.H. Wiley, G.L. Mayberry: Tracer techniques for the determination of monomer reactivity ratios. IV. Copolymerization characteristics of some divine monomers // J. Polym. Sci., Pt. A: Gen. Papers, 1963, Vol. 1, No. 1, 217-226.

Comparison of the melting behaviour of symmetrically substituted bis-alkenyl diphenyl ethers listed in Table 2 (comparative data, literature values) with that of asymmetrically substitued bis-alkenyl diphenyl ethers of this invention (Table 1, examples 4 through 9) clearly demonstrates the advantage of the compounds of the present invention (cf. Table 1) with respect to their rheological properties indicating superior processability (e.g.blendability with bisimides in the melt). As exemplified here, asymmetrically substituted bis-alkenyl diphenyl ethers of the present invention are low-viscosity liquids at room temperature, whereas symmetric bis-alkenyl diphenyl ethers are crystalline solids.

C. Preparation of Curable Mixtures of this Invention Based on Polymaleimide (II) and Asymmetrically Substituted Bis-Alkenyl Diphenyl Ethers of Formula (I)

The curable mixtures of the invention can be obtained according to the following general processes:
(a) Melt Process
At least one polymaleimide of formula (II), at least one asymmetrically substituted bis-alkenyl diphenyl ether (I) and, if required, at least one additional co-monomer component are melt-blended in a temperature range of 100–120° C. until a homogeneous mixture is obtained. Subsequently, the melt thus obtained is further heated in the same temperature range for a time sufficient to obtain a stable melt. Finally, the melt is degassed under reduced pressure of 20 hPa [15 mm Hg] for 2-10 minutes to obtain the curable mixture.
(b) Solvent-Assisted Process
At least one polymaleimide of formula (II) and at least one asymmetrically substituted bis-alkenyl diphenyl ether (I) and, if required, at least one additional co-monomer component and an organic solven, preferably toluene or methylene chloride, in a weight ratio solid-to-solvent of 1:1 are heated up to 90-100° C. until a clear solution is obtained. Subsequently, the solvent is stripped off under reduced pressure, and the temperature is simultaneously increased to between 100-120° C. Finally, the mixture is degassed for 2-10 minutes under reduced pressure of 20 hPa [15 mm Hg] to obtain a curable mixture. The resin/solvent ratio may vary, depending on the solubility of components. Other solvents or diluents, as mentioned in the specification, may also be used.

(c) Reactivity Measurements (c.1) Differential Scanning Calorimetry (DSC)

Differential scanning calorimetric (DSC) traces, obtained at a defined heating rate (10° C./min) in the temperature range from 20 to 380° C., are used to characterize the cure kinetics of curable compositions of the present invention. The cure exothermic maximum, $T_{MAX}$, represents the temperature of maximum heat release at the specified heating rate. The higher is $T_{MAX}$ the slower is the cure of a resin. The $T_{MAX}$ data of curable compositions of polymaleimides of formula (II) and Asymmetrically substituted bis-alkenyl diphenyl ethers of formula (I), prepared in examples 10 through 18, are compiled in Table 3.

(c.2) Hot-Plate Gel Time

Being a standard measure of resin reactivity, the gel time is measured by placing 1 g of the resin on an electrically heated metal block with a polished surface, which is capable of being maintained at temperatures between 130° C. and 230° C., and continuous stirring and probing the molten sample with a wooden rod, as described in the ISO 8987 and ASTM D4217 norms. The gelation results of curable compositions of polymaleimides of formula (II) and asymmetrically substituted bis-alkenyl diphenyl ethers of formula (I), prepared in examples 10 through 18, are compiled in Table 3.

D. Curable Polymaleimide/Asymmetrically Substituted Bis-Alkenyl Diphenyl Ether Mixtures Examples 10 Through 18

TABLE 3

Reactivity data of curable compositions of BMI (II) and asymmetrically substituted bis-alkenyl diphenyl ethers (I). Molar ratio of all BMI (II)/co-monomer (I) mixtures was 1.0:0.7 mol/mol, respectively. DSC heating rate 10° C./min.

| Example No. | Co-monomer (I) from Example No. | Bismaleimide BMI (II) | Reactivity | | |
|---|---|---|---|---|---|
| | | | DSC $T_{MAX}$ (° C.) | Gel time at T (sec) | |
| | | | | 150° C. | 170° C. |
| 10 | 4 | MDAB | 137 | 56 | 10 |
| 11 | 5 | MDAB | 180/220 | 454 | 95 |
| 12 | 5 | C353A | 158s/222 | 2005 | 387 |
| 13 | 5 | 50LM | 163s/228 | 499 | 154 |
| 14 | 6 | MDAB | 195/293 | 1092 | 250 |
| 15 | 7 | MDAB | 178 | 230 | 90 |
| 16 | 7 | C353A | 194 | 1350 | 130 |
| 17 | 8 | MDAB | 194 | 905 | 156 |
| 18 | 9 | MDAB | 172 | 348 | 111 |

MDAB = 4,4'-bismaleimidodiphenylmethane;
C353A = eutectic mixture of 4,4'-bismaleimidodiphenylmethane, 2,4-bismaleimidotoluene, and 1,6-bismaleimido-2,2,4(4,4,2)-trimethylhexane stabilized with hydroquinone, a commercial bismaleimide mixture available from Evonik Industries;
C50LM = eutectic mixture of 4,4'-bismaleimidodiphenylmethane, m-xylylene bismaleimide and 1,6-bismaleimido-2,2,4(4,4,2)-trimethylhexane stabilized with Ionol 46, commercial bismaleimide mixture available from Evonic Industries.

Comparative Examples 19 Through 21

TABLE 4

Comparative reactivity data of BMI(II)/commercial co-monomer mixtures. Molar ratio of all BMI (II)/co-monomer comparative mixtures was 1.0:0.7 mol/mol, respectively. DSC heating rate 10° C./min.

| Example No. | Comparative co-monomer | Bismaleimide BMI (II) | Reactivity | | |
|---|---|---|---|---|---|
| | | | DSC $T_{MAX}$ (° C.) | Gel time at T (sec) | |
| | | | | 150° C. | 170° C. |
| 19 | TM123 | MDAB | 229* | 2768 | 372 |
| 20 | TM123 | C353A | 236* | 4500 | 1478 |
| 21 | TM124 | MDAB | 257* | 5160 | 1810 |

*largest peak
TM124 = o,o'-diallylbisphenol-A (commercial product available from Evonik Industries);
TM123 = 4,4'-bis(o-propenylphenoxy)benzophenone (commercial product available from Evonik Industries);
MDAB = 4,4'-bismaleimidodiphenylmethane.
C353A = eutectic mixture of 4,4'-bismaleimidodiphenylmethane, 2,4-bismaleimidotoluene, and 1,6-bismaleimido-2,2,4(4,4,2)-trimethylhexane stabilized with hydroquinone, commercial bismaleimide mixture available from Evonik Industries.

Comparison of gel time data of examples 10 to 18 (Table 3) with the corresponding gel time data of examples 19 to 21 (mixtures based on commercial co-monomers, Table 4) clearly demonstrates significantly faster curing obtained for the mixtures comprising the asymmetrically substituted bis-alkenyl diphenyl ether (I) type co-monomers of this invention. The results obtained by differential scanning calorimetry (DSC), are in accord with the results obtained from gel time measurements. DSC maxima of the corresponding formulations, $T_{max}$, were found at lower temperatures, for the faster curing mixtures comprising the asymmetrically substituted bis-alkenyl diphenyl ether (I) type co-monomers of this invention.

While the invention has been described in detail, modifications in the spirit and scope of the invention will be readily apparent to those of skill in the art. Those of ordinary skill in the art will appreciate that the foregoing description is by way of example only, and is not intended to limit the invention.

The invention claimed is:

1. An asymmetrically substituted bis-alkenyl diphenyl ether of formula (I):

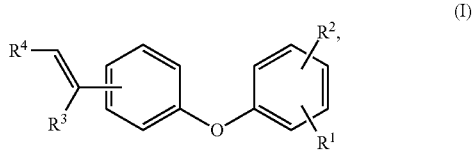

wherein $R^1$ is an 1-alkenyl- or 2-alkenyl group with 3 to 6 carbon atoms, $R^2$ is hydrogen or an alkoxy group with up to 2 carbon atoms, $R^3$ is hydrogen or an alkyl group with up to 4 carbon atoms, and $R^4$ is hydrogen or an alkyl group with up to 4 carbon atoms, with the proviso that (I) is not a naturally occurring ottomentosa (1-methoxy-4-(1E)-1-propen-1-yl-2-[4-(1E)-1-propen-1-ylphenoxy]-benzene).

2. The asymmetrically substituted bis-alkenyl diphenyl ether according to claim 1, wherein the asymmetrically substituted bis-alkenyl diphenyl ether is a compound of formula (Ia):

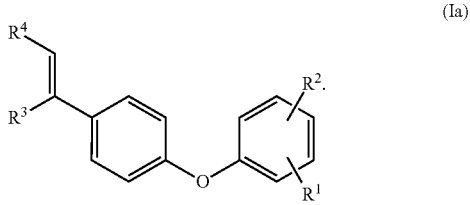

(Ia)

3. The asymmetrically substituted bis-alkenyl diphenyl ether according to claim 2, wherein the asymmetrically substituted bis-alkenyl diphenyl ether is
4-vinyl-2'-(prop-1-en-1-yl)-diphenylether,
4-isopropenyl-2'-(prop-1-en-1-yl)-diphenylether,
4-(prop-1-en-1-yl)-2'-(prop-1-en-1-yl)-diphenylether,
4-(but-1-en-1-yl)-2'-(prop-1-en-1-yl)-diphenylether,
4-(pent-1-en-1-yl)-2'-(prop-1-en-1-yl)-diphenylether,
4-(1-methylprop-1-en-1-yl)-2'-(prop-1-en-1-yl)-diphenylether,
4-(1-methylbut-1-en-1-yl)-2'-(prop-1-en-1-yl)-diphenylether,
4-(1-methylpent-1-en-1-yl)-2'-(prop-1-en-1-yl)-diphenylether,
4-(1-ethylprop-1-en-1-yl)-2'-(prop-1-en-1-yl)-diphenylether,
4-(1-ethylbut-1-en-1-yl)-2'-(prop-1-en-1-yl)-diphenylether,
4-(1-ethylpent-1-en-1-yl)-2'-(prop-1-en-1-yl)-diphenylether,
4-vinyl-2'-methoxy-4'-(prop-1-en-1-yl)-diphenylether,
4-isopropenyl-2'-methoxy-4'-(prop-1-en-1-yl)-diphenylether,
4-(prop-1-en-1-yl)-2'-methoxy-4'-(prop-1-en-1-yl)-diphenylether,
4-(but-1-en-1-yl)-2'-methoxy-4'-(prop-1-en-1-yl)-diphenylether,
4-(pent-1-en-1-yl)-2'-methoxy-4'-(prop-1-en-1-yl)-diphenylether,
4-(1-methylprop-1-en-1-yl)-2'-methoxy-4'-(prop-1-en-1-yl)-diphenylether,
4-(1-methylbut-1-en-1-yl)-2'-methoxy-4'-(prop-1-en-1-yl)-diphenylether,
4-(1-methylpent-1-en-1-yl)-2'-methoxy-4'-(prop-1-en-1-yl)-diphenylether,
4-(1-ethylprop-1-en-1-yl)-2'-methoxy-4'-(prop-1-en-1-yl)-diphenylether,
4-(1-ethylbut-1-en-1-yl)-2'-methoxy-4'-(prop-1-en-1-yl)-diphenylether,
4-(1-ethylpent-1-en-1-yl)-2'-methoxy-4'-(prop-1-en-1-yl)-diphenylether,
4-vinyl-2'-ethoxy-5'-(prop-1-en-1-yl)-diphenylether,
4-isopropenyl-2'-ethoxy-5'-(prop-1-en-1-yl)-diphenylether,
4-(prop-1-en-1-yl)-2'-ethoxy-5'-(prop-1-en-1-yl)-diphenylether,
4-(but-1-en-1-yl)-2'-ethoxy-5'-(prop-1-en-1-yl)-diphenylether,
4-(pent-1-en-1-yl)-2'-ethoxy-5'-(prop-1-en-1-yl)-diphenylether,
4-(1-methylprop-1-en-2-yl)-2'-ethoxy-5'-(prop-1-en-1-yl)-diphenylether,
4-(1-methylbut-1-en-1-yl)-2'-ethoxy-5'-(prop-1-en-1-yl)-diphenylether,
4-(1-methylpent-1-en-1-yl)-2'-ethoxy-5'-(prop-1-en-1-yl)-diphenylether,
4-(1-ethylprop-1-en-1-yl)-2'-ethoxy-5'-(prop-1-en-1-yl)-diphenylether,
4-(1-ethylbut-1-en-1-yl)-2'-ethoxy-5'-(prop-1-en-1-yl)-diphenylether, or
4-(1-ethylpent-1-en-1-yl)-2'-ethoxy-5'-(prop-1-en-1-yl)-diphenylether.

4. The asymmetrically substituted bis-alkenyl diphenyl ether according to claim 1, wherein the asymmetrically substituted bis-alkenyl diphenyl ether is a compound of formula (Ib):

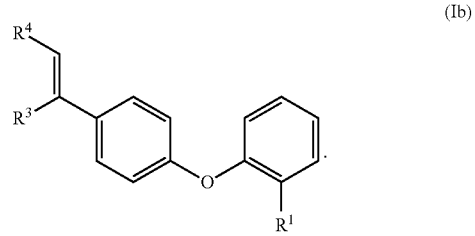

(Ib)

5. The asymmetrically substituted bis-alkenyl diphenyl ether according to claim 4, wherein the asymmetrically substituted bis-alkenyl diphenyl ether is
4-vinyl-2'-(prop-1-en-1-yl)-diphenylether,
4-isopropenyl-2'-(prop-1-en-1-yl)-diphenylether,
4-(prop-1-en-1-yl)-2'-(prop-1-en-1-yl)-diphenylether,
4-(but-1-en-1-yl)-2'-(prop-1-en-1-yl)-diphenylether,
4-(pent-1-en-1-yl)-2'-(prop-1-en-1-yl)-diphenylether,
4-(1-methylprop-1-en-1-yl)-2'-(prop-1-en-1-yl)-diphenylether,
4-(1-methylbut-1-en-1-yl)-2'-(prop-1-en-1-yl)-diphenylether,
4-(1-methylpent-1-en-1-yl)-2'-(prop-1-en-1-yl)-diphenylether,
4-(1-ethylprop-1-en-1-yl)-2'-(prop-1-en-1-yl)-diphenylether,
4-(1-ethylbut-1-en-1-yl)-2'-(prop-1-en-1-yl)-diphenylether, or
4-(1-ethylpent-1-en-1-yl)-2'-(prop-1-en-1-yl)-diphenylether.

6. The asymmetrically substituted bis-alkenyl diphenyl ether according to claim 1, wherein the asymmetrically substituted bis-alkenyl diphenyl ether is a compound of formula (Ic):

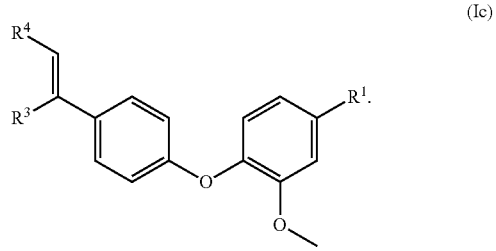

(Ic)

7. The asymmetrically substituted bis-alkenyl diphenyl ether according to claim 6, wherein the asymmetrically substituted bis-alkenyl ether is 4-vinyl-2'-methoxy-4'-(prop-1-en-1-yl)-diphenylether,
4-isopropenyl-2'-methoxy-4'-(prop-1-en-1-yl)-diphenylether,
4-(prop-1-en-1-yl)-2'-methoxy-4'-(prop-1-en-1-yl)-diphenylether,
4-(but-1-en-1-yl)-2'-methoxy-4'-(prop-1-en-1-yl)-diphenylether,
4-(pent-1-en-1-yl)-2'-methoxy-4'-(prop-1-en-1-yl)-diphenylether,
4-(1-methylprop-1-en-1-yl)-2'-methoxy-4'-(prop-1-en-1-yl)-diphenylether,
4-(1-methylbut-1-en-1-yl)-2'-methoxy-4'-(prop-1-en-1-yl)-diphenylether,
4-(1-methylpent-1-en-1-yl)-2'-methoxy-4'-(prop-1-en-1-yl)-diphenylether,
4-(1-ethylprop-1-en-1-yl)-2'-methoxy-4'-(prop-1-en-1-yl)-diphenylether,
4-(1-ethylbut-1-en-1-yl)-2'-methoxy-4'-(prop-1-en-1-yl)-diphenylether, or
4-(1-ethylpent-1-en-1-yl)-2'-methoxy-4'-(prop-1-en-1-yl)-diphenylether.

8. The asymmetrically substituted bis-alkenyl diphenyl ether according to claim 1, wherein the asymmetrically substituted bis-alkenyl diphenyl ether is a compound of formula (Id):

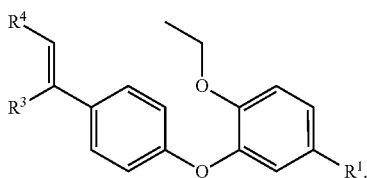

9. The asymmetrically substituted bis-alkenyl diphenyl ether according to claim 8, wherein the asymmetrically substituted bis-alkenyl diphenyl ether is
4-vinyl-2'-ethoxy-5'-(prop-1-en-1-yl)-diphenylether,
4-isopropenyl-2'-ethoxy-5'-(prop-1-en-1-yl)-diphenyiether,
4-(prop-1-en-1-yl)-2'-ethoxy-5'-(prop-1-en-1-yl)-diphenylether,
4-(but-1-en-1-yl)-2'-ethoxy-5'-(prop-1-en-1-yl)-diphenylether,
4-(pent-1-en-1-yl)-2'-ethoxy-5'-(prop-1-en-1-yl)-diphenylether,
4-(1-methylprop-1-en-1-yl)-2'-ethoxy-5'-(prop-1-en-1-yl)-diphenylether,
4-(1-methylbut-1-en-1-yl)-2'-ethoxy-5'-(prop-1-en-1-yl)-diphenylether,
4-(1-methylpent-1-en-1-yl)-2'-ethoxy-5'-(prop-1-en-1-yl)-diphenylether,
4-(1-ethylprop-1-en-1-yl)-2'-ethoxy-5'-(prop-1-en-1-yl)-diphenylether,
4-(1-ethylbut-1-en-1-yl)-2'-ethoxy-5'-(prop-1-en-1-yl)-diphenylether, or
4-(1-ethylpent-1-en-1-yl)-2'-ethoxy-5'-(prop-1-en-1-yl)-diphenylether.

10. A curable composition, comprising:
(a) an asymmetrically substituted bis-alkenyl diphenyl ether according to claim 1;

(b) a polyimide of formula (II):

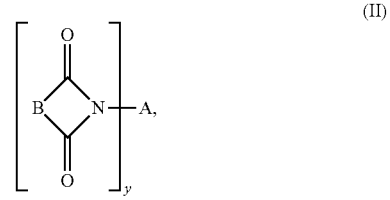

wherein B is a difunctional group containing a carbon-carbon double bond,
A is a y-functional group, wherein the y-functional group denotes a group bonded to the reminder of the polyimide of formula (II) via y bonds, and
y is an integer ≥2.

11. The curable composition according to claim 10, wherein B in the polyimide of formula (II) is

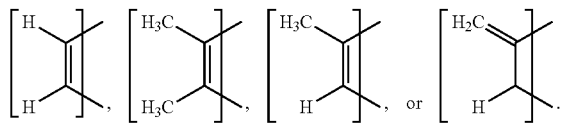

12. The curable composition according to claim 10, wherein A in the polyimide of formula (II) is
a) an alkylene group with 2 to 12 carbon atoms;
b) a cycloalkylene group with 5 to 6 carbon atoms;
c) a heterocyclic group with 4 to 5 carbon atoms and at least one nitrogen, oxygen, or sulphur atom in the ring;
d) a mono- or dicarbocyclic group;
e) a bridged multicyclic group consisting of at least two selected from the group consisting of: a monocarbocyclic aromatic group, a dicarbocyclic aromatic group, and a cycloalkylene group; wherein these groups are linked to each other by direct carbon-carbon bonds or by divalent groups; or
f) a group of formula (III)

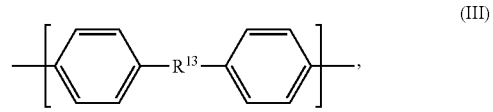

wherein $R^{13}$ is

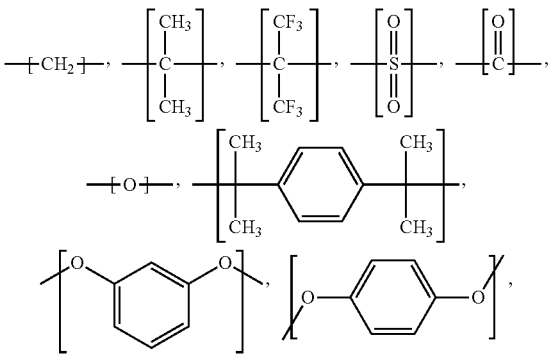

-continued

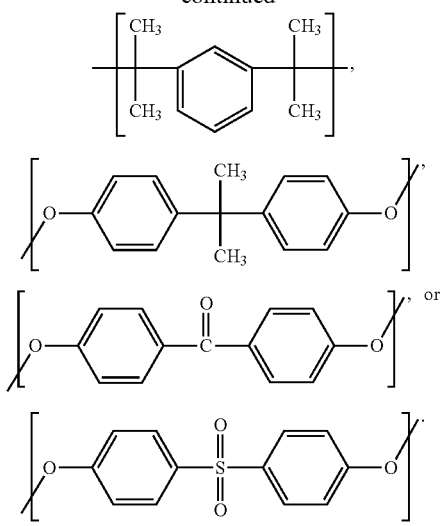

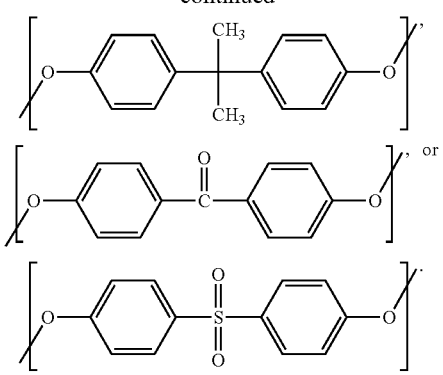

13. The curable composition according claim 10, in which the polyimide of formula (II) is a bisimide of formula (XVIII):

(XVIII)

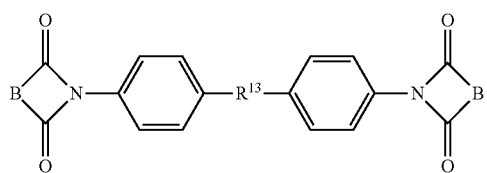

wherein $R^{13}$ is

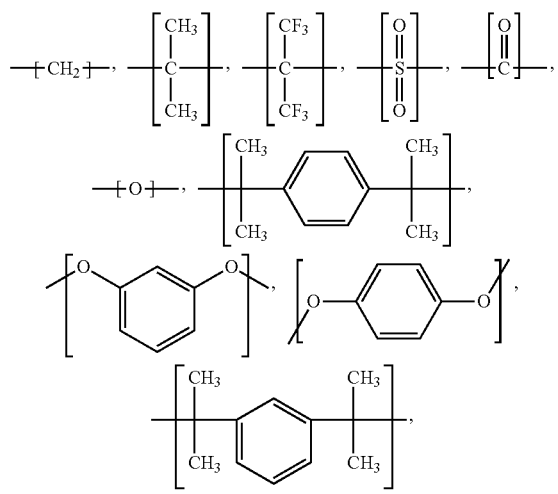

14. The curable composition according to claim 10, in which the polyimide of formula (II) is a bismaleimide selected from the group consisting of:

4,4'-bismaleimidodiphenylmethane, bis(3-methyl-5-ethyl-4-maleimidophenyl)methane, bis(3,5-dimethyl-4-maleimidophenyl)methane, 4,4'-bismaleimidodiphenylether, 4,4'-bismaleimidodiphenylsulfone, 3,3'-bismaleimidodiphenylsulfone, bismaleimidodiphenylindane, 2,4-bismaleimidotoluene, 2,6-bismaleimidotoluene, 1,3-bismaleimidobenzene, 1,2-bismaleimidobenzene, 1,4-bismaleimidobenzene, 1,2-bismaleimidoethane, 1,6-bismaleimidohexane, 1,6-bismaleimido-(2,2,4-trimethyl)hexane, 1,6-bismaleimido-(2,4,4-trimethyl) hexane, 1,4-bis(maleimidomethyl)cyclohexane, 1,3-bis(maleimidomethyl)cyclohexane, 1,4-bismaleimidodicyclohexylmethane, and 1,3-bis(maleimidomethyl)benzene, 1,4-bis(maleimidomethyl) benzene.

15. A process for manufacturing the curable composition according to claim 10, the process comprising:

blending components of the curable composition using a powder-, melt-, or solvent-assisted blending process resulting in a curable composition that is solid, low-melting, or tacky.

16. A curable prepolymer obtained from the curable composition according to claim 10, by a process comprising:

heating the curable composition to a temperature of from 50° C. to 250° C., for a time sufficient to obtain a curable prepolymer, which is still polymerizable upon application of heat and/or pressure.

17. A crosslinked polymer obtained from the curable composition according to claim 10 by a process comprising heating the curable composition to a temperature of from 70° C. to 280° C. for a time sufficient to obtain the crosslinked polymer.

18. A process for manufacturing a composite material, the process comprising:

combining the curable composition according to claim 10 with a fibrous or particulate reinforcement and curing the resultant product.

19. A composite material obtained by the process according to claim 18.

\* \* \* \* \*